(12) United States Patent
Metzger et al.

(10) Patent No.: US 8,500,818 B2
(45) Date of Patent: *Aug. 6, 2013

(54) KNEE PROSTHESIS ASSEMBLY WITH LIGAMENT LINK

(75) Inventors: Robert Metzger, Wakarusa, IN (US); Brian A. Uthgenannt, Winona Lake, IN (US); Kevin T. Stone, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 41 days.

This patent is subject to a terminal disclaimer.

(21) Appl. No.: 12/788,973

(22) Filed: May 27, 2010

(65) Prior Publication Data

US 2010/0305709 A1    Dec. 2, 2010

Related U.S. Application Data

(63) Continuation-in-part of application No. 12/489,168, filed on Jun. 22, 2009, now Pat. No. 8,361,113, which is a continuation-in-part of application No. 12/474,802, filed on May 29, 2009, now Pat. No. 8,088,130, which is a continuation-in-part of application No. 12/196,405, filed on Aug. 22, 2008, (Continued)

(51) Int. Cl.
*A61F 2/38* (2006.01)

(52) U.S. Cl.
USPC .................. 623/20.31; 623/20.28; 623/20.14; 623/13.12

(58) Field of Classification Search
USPC ........... 623/13.12, 20.14, 0.21, 20.22, 20.24, 623/20.26, 20.28, 20.29, 20.33, 23.41
See application file for complete search history.

(56) References Cited

U.S. PATENT DOCUMENTS

| 65,499 A | 6/1867 | Miller |
|---|---|---|
| 126,366 A | 4/1872 | Wills |

(Continued)

FOREIGN PATENT DOCUMENTS

| AU | 4957264 | 3/1966 |
|---|---|---|
| AU | 440266 | 10/1967 |

(Continued)

OTHER PUBLICATIONS

US 6,238,418, 5/2001, Schwartz et al. (withdrawn).

(Continued)

*Primary Examiner* — David Isabella
*Assistant Examiner* — Marcia Hoffman
(74) *Attorney, Agent, or Firm* — Harness, Dickey

(57) ABSTRACT

A prosthetic knee joint assembly includes a femoral component and a bearing that supports articulation of the femoral component. The assembly further includes a tibial tray. Furthermore, the assembly includes a ligament link operably coupled to the tibial tray or the femoral component via a coupling component. The ligament link extending through the other of the tibial tray or the femoral component to couple to the respective one of the femur or tibia. The ligament link extends between first and second ends and includes an outer wall defining an interior longitudinal passage portion. First and second apertures extend through the wall. The first end extends through the first and second apertures and the longitudinal passage portion to define a first adjustable loop, and the second end extends through the first and second apertures and the longitudinal passage portion to define a second adjustable loop.

20 Claims, 12 Drawing Sheets

Related U.S. Application Data now Pat. No. 8,128,658, and a continuation-in-part of application No. 12/196,407, filed on Aug. 22, 2008, now Pat. No. 8,137,382, and a continuation-in-part of application No. 12/196,410, filed on Aug. 22, 2008, now Pat. No. 8,118,836, and a continuation-in-part of application No. 11/541,506, filed on Sep. 29, 2006, now Pat. No. 7,601,165, application No. 12/788,973, which is a continuation-in-part of application No. 12/570,854, filed on Sep. 30, 2009, now Pat. No. 8,303,604, which is a continuation-in-part of application No. 12/014,399, filed on Jan. 15, 2008, now Pat. No. 7,909,851, and a continuation-in-part of application No. 12/014,340, filed on Jan. 15, 2008, now Pat. No. 7,905,904, application No. 12/788,973, which is a continuation-in-part of application No. 12/702,067, filed on Feb. 8, 2010, which is a continuation of application No. 11/541,505, filed on Sep. 29, 2006, now Pat. No. 7,658,751, application No. 12/788,973, which is a continuation-in-part of application No. 12/196,398, filed on Aug. 22, 2008, now Pat. No. 7,959,650, which is a continuation-in-part of application No. 11/784,821, filed on Apr. 10, 2007.

(60) Provisional application No. 61/181,938, filed on May 28, 2009.

(56) References Cited

U.S. PATENT DOCUMENTS

| | | | |
|---|---|---|---|
| 233,475 | A | 10/1880 | Cook et al. |
| 261,501 | A | 7/1882 | Vandermark |
| 268,407 | A | 12/1882 | Hughes |
| 330,087 | A | 11/1885 | Binns |
| 417,805 | A | 12/1889 | Beaman |
| 487,304 | A | 12/1892 | Todd |
| 762,710 | A | 6/1901 | Hall |
| 837,767 | A | 12/1906 | Aims |
| 838,203 | A | 12/1906 | Neil |
| 1,059,631 | A | 4/1913 | Popovics |
| 1,131,155 | A | 3/1915 | Murphy |
| 1,153,450 | A | 9/1915 | Schaff |
| 1,346,940 | A | 7/1920 | Collins |
| 1,635,066 | A | 7/1927 | Wells |
| 1,950,799 | A | 3/1934 | Jones |
| 2,065,659 | A | 12/1936 | Cullen |
| 2,108,206 | A | 2/1938 | Meeker |
| 2,121,193 | A | 6/1938 | Hanicke |
| 2,242,003 | A | 5/1941 | Lorenzo |
| 2,267,925 | A | 12/1941 | Johnston |
| 2,302,986 | A | 11/1942 | Vollrath |
| 2,329,398 | A | 9/1943 | Duffy |
| RE22,857 | E | 3/1947 | Ogburn |
| 2,526,959 | A | 10/1950 | Lorenzo |
| 2,528,456 | A | 10/1950 | Stevenson |
| 2,562,419 | A | 7/1951 | Ferris |
| 2,581,564 | A | 1/1952 | Villegas |
| 2,600,395 | A | 6/1952 | Domoj et al. |
| 2,610,631 | A | 9/1952 | Calicchio |
| 2,665,597 | A | 1/1954 | Hill |
| 2,669,774 | A | 2/1954 | Mitchell |
| 2,698,986 | A | 1/1955 | Brown |
| 2,760,488 | A | 8/1956 | Pierce |
| 2,833,284 | A | 5/1958 | Springer |
| 2,846,712 | A | 8/1958 | Markman |
| 2,860,393 | A | 11/1958 | Brock |
| 2,880,728 | A | 4/1959 | Rights |
| 2,881,762 | A | 4/1959 | Lowrie |
| 2,883,096 | A | 4/1959 | Dawson |
| 2,913,042 | A | 11/1959 | Taylor |
| 3,000,009 | A | 9/1961 | Selstad |
| 3,003,155 | A | 10/1961 | Mielzynski et al. |
| 3,013,559 | A | 12/1961 | Thomas |
| 3,037,619 | A | 6/1962 | Stevans |
| 3,039,460 | A | 6/1962 | Chandler |
| 3,090,386 | A | 5/1963 | Curtis |
| 3,103,666 | A | 9/1963 | Bone |
| 3,123,077 | A | 3/1964 | Alcamo |
| 3,125,095 | A | 3/1964 | Kaufman et al. |
| 3,209,422 | A | 10/1965 | Dritz |
| 3,234,938 | A | 2/1966 | Robinson |
| 3,240,379 | A | 3/1966 | Bremer et al. |
| 3,250,271 | A | 5/1966 | Lippes |
| 3,399,432 | A | 9/1968 | Merser |
| 3,409,014 | A | 11/1968 | Shannon |
| RE26,501 | E | 12/1968 | Kendrick et al. |
| 3,435,475 | A | 4/1969 | Bisk |
| 3,467,089 | A | 9/1969 | Hasson |
| 3,470,834 | A | 10/1969 | Bone |
| 3,470,875 | A | 10/1969 | Johnson |
| 3,500,820 | A | 3/1970 | Almen |
| 3,507,274 | A | 4/1970 | Soichet |
| 3,513,484 | A | 5/1970 | Hausner |
| 3,515,132 | A | 6/1970 | McKnight |
| 3,522,803 | A | 8/1970 | Majzlin |
| 3,527,223 | A | 9/1970 | Shein |
| 3,533,406 | A | 10/1970 | Hutterer et al. |
| 3,541,591 | A | 11/1970 | Hoegerman |
| 3,547,389 | A | 12/1970 | Mitchell |
| 3,579,831 | A | 5/1971 | Stevens et al. |
| 3,590,616 | A | 7/1971 | Schussler et al. |
| 3,608,095 | A | 9/1971 | Barry |
| 3,618,447 | A | 11/1971 | Goins |
| 3,628,530 | A | 12/1971 | Schwartz |
| 3,643,649 | A | 2/1972 | Amato |
| 3,648,705 | A | 3/1972 | Lary |
| 3,656,483 | A | 4/1972 | Rudel |
| 3,659,597 | A | 5/1972 | Wolfers |
| 3,664,345 | A | 5/1972 | Dabbs et al. |
| 3,665,560 | A | 5/1972 | Bennett et al. |
| 3,675,639 | A | 7/1972 | Cimber |
| 3,683,422 | A | 8/1972 | Stemmer et al. |
| 3,692,022 | A | 9/1972 | Ewing |
| 3,695,271 | A | 10/1972 | Chodorow |
| 3,699,969 | A | 10/1972 | Allen |
| 3,716,058 | A | 2/1973 | Tanner, Jr. |
| 3,744,488 | A | 7/1973 | Cox |
| 3,752,516 | A | 8/1973 | Mumma |
| 3,757,629 | A | 9/1973 | Schneider |
| 3,763,856 | A | 10/1973 | Blomberg |
| 3,771,520 | A | 11/1973 | Lerner |
| 3,777,748 | A | 12/1973 | Abramson |
| 3,807,407 | A | 4/1974 | Schweizer |
| 3,810,456 | A | 5/1974 | Karman |
| 3,825,010 | A | 7/1974 | McDonald |
| 3,840,017 | A | 10/1974 | Violante et al. |
| 3,842,824 | A | 10/1974 | Neufeld |
| 3,842,840 | A | 10/1974 | Schweizer |
| 3,845,772 | A | 11/1974 | Smith |
| 3,867,933 | A | 2/1975 | Kitrilakis |
| 3,867,944 | A | 2/1975 | Samuels |
| 3,871,368 | A | 3/1975 | Johnson et al. |
| 3,871,379 | A | 3/1975 | Clarke |
| 3,874,388 | A | 4/1975 | King et al. |
| 3,875,648 | A | 4/1975 | Bone |
| 3,877,570 | A | 4/1975 | Barry |
| 3,880,156 | A | 4/1975 | Hoff |
| 3,881,475 | A | 5/1975 | Gordon et al. |
| 3,889,666 | A | 6/1975 | Lerner |
| 3,892,240 | A | 7/1975 | Park |
| 3,896,500 | A | 7/1975 | Rambert et al. |
| 3,907,442 | A | 9/1975 | Reid |
| 3,910,281 | A | 10/1975 | Kletschka et al. |
| 3,918,444 | A | 11/1975 | Hoff et al. |
| 3,918,455 | A | 11/1975 | Coplan |
| 3,927,666 | A | 12/1975 | Hoff |
| 3,931,667 | A | 1/1976 | Merser et al. |
| 3,933,153 | A | 1/1976 | Csatary et al. |
| 3,937,217 | A | 2/1976 | Kosonen et al. |
| 3,943,932 | A | 3/1976 | Woo |

| Patent No. | Kind | Date | Inventor |
|---|---|---|---|
| 3,946,446 | A | 3/1976 | Schofield |
| 3,946,728 | A | 3/1976 | Bettex et al. |
| 3,946,740 | A | 3/1976 | Bassett |
| 3,953,896 | A | 5/1976 | Treace |
| 3,954,103 | A | 5/1976 | Garcia-Roel et al. |
| 3,961,632 | A | 6/1976 | Moossun |
| 3,973,560 | A | 8/1976 | Emmett et al. |
| 3,976,079 | A | 8/1976 | Samuels et al. |
| 3,977,050 | A | 8/1976 | Perez et al. |
| 3,979,799 | A | 9/1976 | Merser et al. |
| 3,985,138 | A | 10/1976 | Jarvik |
| 3,990,619 | A | 11/1976 | Russell |
| 4,005,707 | A | 2/1977 | Moulding, Jr. |
| 4,006,747 | A | 2/1977 | Kronenthal et al. |
| 4,007,743 | A | 2/1977 | Blake |
| 4,013,071 | A | 3/1977 | Rosenberg et al. |
| 4,026,281 | A | 5/1977 | Mayberry et al. |
| 4,036,101 | A | 7/1977 | Burnett |
| 4,050,100 | A | 9/1977 | Barry |
| 4,054,954 | A | 10/1977 | Nakayama et al. |
| 4,085,466 | A | 4/1978 | Goodfellow et al. |
| 4,094,313 | A | 6/1978 | Komamura et al. |
| 4,099,750 | A | 7/1978 | McGrew |
| 4,103,690 | A | 8/1978 | Harris |
| RE29,819 | E | 10/1978 | Bone |
| 4,121,487 | A | 10/1978 | Bone |
| 4,143,656 | A | 3/1979 | Holmes et al. |
| 4,144,876 | A | 3/1979 | DeLeo |
| 4,149,277 | A | 4/1979 | Bokros |
| 4,157,714 | A | 6/1979 | Foltz et al. |
| 4,160,453 | A | 7/1979 | Miller |
| 4,164,225 | A | 8/1979 | Johnson et al. |
| 4,172,458 | A | 10/1979 | Pereyra |
| 4,175,555 | A | 11/1979 | Herbert et al. |
| 4,185,636 | A | 1/1980 | Gabbay et al. |
| 4,196,883 | A | 4/1980 | Einhorn et al. |
| 4,210,148 | A | 7/1980 | Stivala |
| 4,235,161 | A | 11/1980 | Kunreuther |
| 4,235,238 | A | 11/1980 | Ogiu et al. |
| 4,237,779 | A | 12/1980 | Kunreuther |
| 4,243,037 | A | 1/1981 | Smith |
| 4,249,525 | A | 2/1981 | Krzeminski |
| 4,263,913 | A | 4/1981 | Malmin |
| 4,265,246 | A | 5/1981 | Barry |
| 4,273,117 | A | 6/1981 | Neuhauser |
| 4,275,717 | A | 6/1981 | Bolesky |
| 4,287,807 | A | 9/1981 | Pacharis et al. |
| 4,291,698 | A | 9/1981 | Fuchs et al. |
| 4,301,551 | A | 11/1981 | Dore et al. |
| 4,307,723 | A | 12/1981 | Finney |
| 4,312,337 | A | 1/1982 | Donohue |
| 4,316,469 | A | 2/1982 | Kapitanov |
| 4,326,531 | A | 4/1982 | Shimonaka |
| 4,345,601 | A | 8/1982 | Fukuda |
| 4,349,027 | A | 9/1982 | DiFrancesco |
| 4,388,921 | A | 6/1983 | Sutter et al. |
| 4,400,833 | A | 8/1983 | Kurland |
| 4,402,445 | A | 9/1983 | Green |
| 4,409,974 | A | 10/1983 | Freedland |
| 4,438,769 | A | 3/1984 | Pratt et al. |
| 4,441,489 | A | 4/1984 | Evans et al. |
| 4,454,875 | A | 6/1984 | Pratt et al. |
| 4,462,395 | A | 7/1984 | Johnson |
| 4,463,753 | A | 8/1984 | Gustilo |
| 4,473,102 | A | 9/1984 | Ohman et al. |
| 4,484,570 | A | 11/1984 | Sutter et al. |
| 4,489,446 | A | 12/1984 | Reed |
| 4,493,323 | A | 1/1985 | Albright et al. |
| 4,496,468 | A | 1/1985 | House et al. |
| 4,505,274 | A | 3/1985 | Speelman |
| 4,509,516 | A | 4/1985 | Richmond |
| 4,531,522 | A | 7/1985 | Bedi et al. |
| 4,532,926 | A | 8/1985 | O'Holla |
| 4,534,350 | A | 8/1985 | Golden et al. |
| 4,535,764 | A | 8/1985 | Ebert |
| 4,537,185 | A | 8/1985 | Stednitz |
| 4,549,545 | A | 10/1985 | Levy |
| 4,549,652 | A | 10/1985 | Free |
| 4,561,432 | A | 12/1985 | Mazor |
| 4,564,007 | A | 1/1986 | Coombs et al. |
| 4,570,623 | A | 2/1986 | Ellison et al. |
| 4,573,844 | A | 3/1986 | Smith |
| 4,576,608 | A | 3/1986 | Homsy |
| 4,584,722 | A | 4/1986 | Levy et al. |
| 4,590,928 | A | 5/1986 | Hunt et al. |
| 4,595,007 | A | 6/1986 | Mericle |
| 4,596,249 | A | 6/1986 | Freda et al. |
| 4,602,635 | A | 7/1986 | Mulhollan et al. |
| 4,602,636 | A | 7/1986 | Noiles |
| 4,604,997 | A | 8/1986 | De Bastiani et al. |
| 4,605,414 | A | 8/1986 | Czajka |
| 4,616,650 | A | 10/1986 | Green et al. |
| 4,621,640 | A | 11/1986 | Mulhollan et al. |
| 4,624,254 | A | 11/1986 | McGarry et al. |
| 4,632,100 | A | 12/1986 | Somers et al. |
| 4,635,637 | A | 1/1987 | Schreiber |
| 4,636,121 | A | 1/1987 | Miller |
| 4,641,652 | A | 2/1987 | Hutterer et al. |
| 4,649,952 | A | 3/1987 | Jobe |
| 4,653,486 | A | 3/1987 | Coker |
| 4,653,487 | A | 3/1987 | Maale |
| 4,653,489 | A | 3/1987 | Tronzo |
| 4,655,777 | A | 4/1987 | Dunn et al. |
| 4,662,068 | A | 5/1987 | Polonsky |
| 4,667,662 | A | 5/1987 | Titone et al. |
| 4,667,675 | A | 5/1987 | Davis |
| 4,669,473 | A | 6/1987 | Richards et al. |
| 4,683,895 | A | 8/1987 | Pohndorf |
| 4,688,561 | A | 8/1987 | Reese |
| 4,690,169 | A | 9/1987 | Jobe |
| 4,696,300 | A | 9/1987 | Anderson |
| 4,705,040 | A | 11/1987 | Mueller et al. |
| 4,708,132 | A | 11/1987 | Silvestrini |
| 4,714,475 | A | 12/1987 | Grundei et al. |
| 4,716,893 | A | 1/1988 | Fischer et al. |
| 4,719,671 | A | 1/1988 | Ito et al. |
| 4,719,917 | A | 1/1988 | Barrows et al. |
| 4,723,540 | A | 2/1988 | Gilmer, Jr. |
| 4,724,839 | A | 2/1988 | Bedi et al. |
| 4,728,332 | A | 3/1988 | Albrektsson |
| 4,738,255 | A | 4/1988 | Goble et al. |
| 4,741,330 | A | 5/1988 | Hayhurst |
| 4,741,336 | A | 5/1988 | Failla et al. |
| 4,744,353 | A | 5/1988 | McFarland |
| 4,744,793 | A | 5/1988 | Parr et al. |
| 4,750,492 | A | 6/1988 | Jacobs |
| 4,760,843 | A | 8/1988 | Fischer et al. |
| 4,760,844 | A | 8/1988 | Kyle |
| 4,760,848 | A | 8/1988 | Hasson |
| 4,770,663 | A | 9/1988 | Hanslik et al. |
| 4,772,261 | A | 9/1988 | Von Hoff et al. |
| 4,772,286 | A | 9/1988 | Goble et al. |
| 4,773,910 | A | 9/1988 | Chen et al. |
| 4,775,380 | A | 10/1988 | Seedhom et al. |
| 4,776,328 | A | 10/1988 | Frey et al. |
| 4,781,190 | A | 11/1988 | Lee |
| 4,784,126 | A | 11/1988 | Hourahane |
| 4,787,882 | A | 11/1988 | Claren |
| 4,790,297 | A | 12/1988 | Luque |
| 4,793,363 | A | 12/1988 | Ausherman et al. |
| 4,809,695 | A | 3/1989 | Gwathmey et al. |
| 4,813,406 | A | 3/1989 | Ogle, II |
| 4,823,794 | A | 4/1989 | Pierce |
| 4,828,562 | A | 5/1989 | Kenna |
| 4,832,026 | A | 5/1989 | Jones |
| 4,834,098 | A | 5/1989 | Jones |
| 4,838,282 | A | 6/1989 | Strasser et al. |
| 4,841,960 | A | 6/1989 | Garner |
| 4,851,005 | A | 7/1989 | Hunt et al. |
| 4,858,608 | A | 8/1989 | McQuilkin |
| 4,860,513 | A | 8/1989 | Whitman |
| 4,863,383 | A | 9/1989 | Grafelmann |
| 4,870,957 | A | 10/1989 | Goble et al. |
| 4,873,976 | A | 10/1989 | Schreiber |
| 4,887,601 | A | 12/1989 | Richards |
| 4,890,615 | A | 1/1990 | Caspari et al. |
| 4,893,619 | A | 1/1990 | Dale et al. |
| 4,893,974 | A | 1/1990 | Fischer et al. |

| Patent No. | Date | Inventor |
|---|---|---|
| 4,895,148 A | 1/1990 | Bays et al. |
| 4,896,668 A | 1/1990 | Popoff et al. |
| 4,898,156 A | 2/1990 | Gatturna et al. |
| 4,899,743 A | 2/1990 | Nicholson et al. |
| 4,901,721 A | 2/1990 | Hakki |
| 4,923,461 A | 5/1990 | Caspari et al. |
| 4,927,421 A | 5/1990 | Goble et al. |
| 4,946,377 A | 8/1990 | Kovach |
| 4,946,468 A | 8/1990 | Li |
| 4,950,270 A | 8/1990 | Bowman et al. |
| 4,950,285 A | 8/1990 | Wilk |
| 4,960,381 A | 10/1990 | Niznick |
| 4,961,741 A | 10/1990 | Hayhurst |
| 4,968,315 A | 11/1990 | Gatturna |
| 4,968,317 A | 11/1990 | Tormala et al. |
| 4,969,886 A | 11/1990 | Cziffer et al. |
| 4,974,488 A | 12/1990 | Spralja |
| 4,976,736 A | 12/1990 | White et al. |
| 4,978,350 A | 12/1990 | Wagenknecht |
| 4,979,956 A | 12/1990 | Silvestrini |
| 4,983,176 A | 1/1991 | Cushman et al. |
| 4,988,351 A | 1/1991 | Paulos et al. |
| 4,994,074 A | 2/1991 | Bezwada et al. |
| 4,997,433 A | 3/1991 | Goble et al. |
| 5,002,550 A | 3/1991 | Li |
| 5,002,562 A | 3/1991 | Oberlander |
| 5,007,921 A | 4/1991 | Brown |
| 5,030,224 A | 7/1991 | Wright et al. |
| 5,030,235 A | 7/1991 | Campbell, Jr. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,047,030 A | 9/1991 | Draenert |
| 5,053,046 A | 10/1991 | Janese |
| 5,053,047 A | 10/1991 | Yoon |
| 5,059,201 A | 10/1991 | Asnis |
| 5,059,206 A | 10/1991 | Winters |
| 5,061,277 A | 10/1991 | Carpentier et al. |
| 5,062,344 A | 11/1991 | Gerker |
| 5,062,843 A | 11/1991 | Mahony, III |
| 5,064,431 A | 11/1991 | Gilbertson et al. |
| 5,074,874 A | 12/1991 | Yoon et al. |
| 5,078,731 A | 1/1992 | Hayhurst |
| 5,078,843 A | 1/1992 | Pratt |
| 5,084,050 A | 1/1992 | Draenert |
| 5,084,058 A | 1/1992 | Li |
| 5,085,661 A | 2/1992 | Moss |
| 5,087,263 A | 2/1992 | Li |
| 5,087,309 A | 2/1992 | Melton, Jr. |
| 5,089,012 A | 2/1992 | Prou |
| 5,092,866 A | 3/1992 | Breard et al. |
| 5,098,435 A | 3/1992 | Stednitz et al. |
| 5,100,415 A | 3/1992 | Hayhurst |
| 5,100,417 A | 3/1992 | Cerier et al. |
| 5,116,337 A | 5/1992 | Johnson |
| 5,116,373 A | 5/1992 | Jakob et al. |
| 5,116,375 A | 5/1992 | Hofmann |
| 5,123,913 A | 6/1992 | Wilk et al. |
| 5,123,914 A | 6/1992 | Cope |
| 5,127,785 A | 7/1992 | Faucher et al. |
| 5,129,901 A | 7/1992 | Decoste |
| 5,129,902 A | 7/1992 | Goble et al. |
| 5,129,904 A | 7/1992 | Illi et al. |
| 5,129,906 A | 7/1992 | Ross et al. |
| 5,139,498 A | 8/1992 | Astudillo Ley |
| 5,139,499 A | 8/1992 | Small et al. |
| 5,139,520 A | 8/1992 | Rosenberg |
| 5,143,498 A | 9/1992 | Whitman |
| 5,147,362 A | 9/1992 | Goble |
| 5,149,329 A | 9/1992 | Richardson |
| 5,152,790 A | 10/1992 | Rosenberg et al. |
| 5,154,189 A | 10/1992 | Oberlander |
| 5,156,616 A | 10/1992 | Meadows et al. |
| 5,163,960 A | 11/1992 | Bonutti |
| D331,626 S | 12/1992 | Hayhurst et al. |
| 5,169,400 A | 12/1992 | Muhling et al. |
| 5,176,682 A | 1/1993 | Chow |
| 5,178,629 A | 1/1993 | Kammerer |
| 5,183,458 A | 2/1993 | Marx |
| 5,192,282 A | 3/1993 | Draenert |
| 5,197,987 A | 3/1993 | Koch et al. |
| 5,203,784 A | 4/1993 | Ross et al. |
| 5,203,787 A | 4/1993 | Noblitt et al. |
| 5,207,679 A | 5/1993 | Li |
| 5,209,753 A | 5/1993 | Biedermann et al. |
| 5,209,805 A | 5/1993 | Spraggins |
| 5,211,647 A | 5/1993 | Schmieding |
| 5,211,650 A | 5/1993 | Noda |
| 5,214,987 A | 6/1993 | Fenton, Sr. |
| 5,219,359 A | 6/1993 | McQuilkin et al. |
| 5,222,976 A | 6/1993 | Yoon |
| 5,224,946 A | 7/1993 | Hayhurst et al. |
| 5,230,699 A | 7/1993 | Grasinger |
| 5,232,436 A | 8/1993 | Janevski |
| 5,234,435 A | 8/1993 | Seagrave, Jr. |
| 5,235,238 A | 8/1993 | Nomura et al. |
| 5,236,445 A | 8/1993 | Hayhurst et al. |
| 5,236,461 A | 8/1993 | Forte |
| 5,242,447 A | 9/1993 | Borzone |
| 5,246,441 A | 9/1993 | Ross et al. |
| 5,249,899 A | 10/1993 | Wilson |
| 5,250,053 A | 10/1993 | Snyder |
| 5,258,015 A | 11/1993 | Li et al. |
| 5,258,016 A | 11/1993 | DiPoto et al. |
| 5,258,040 A | 11/1993 | Bruchman et al. |
| 5,261,908 A | 11/1993 | Campbell, Jr. |
| 5,268,001 A | 12/1993 | Nicholson et al. |
| 5,269,160 A | 12/1993 | Wood |
| 5,269,783 A | 12/1993 | Sander |
| 5,269,806 A | 12/1993 | Sardelis et al. |
| 5,269,809 A | 12/1993 | Hayhurst et al. |
| 5,279,311 A | 1/1994 | Snyder |
| 5,281,422 A | 1/1994 | Badylak et al. |
| 5,282,809 A | 2/1994 | Kammerer et al. |
| 5,282,832 A | 2/1994 | Toso et al. |
| 5,282,867 A | 2/1994 | Mikhail |
| 5,285,040 A | 2/1994 | Brandberg et al. |
| 5,290,217 A | 3/1994 | Campos |
| 5,306,301 A | 4/1994 | Graf et al. |
| 5,312,422 A | 5/1994 | Trott |
| 5,312,438 A | 5/1994 | Johnson |
| 5,318,566 A | 6/1994 | Miller |
| 5,318,575 A | 6/1994 | Chesterfield et al. |
| 5,318,577 A | 6/1994 | Li |
| 5,318,578 A | 6/1994 | Hasson |
| 5,320,115 A | 6/1994 | Kenna |
| 5,320,626 A | 6/1994 | Schmieding |
| 5,320,633 A | 6/1994 | Allen et al. |
| 5,324,308 A | 6/1994 | Pierce |
| 5,330,489 A | 7/1994 | Green et al. |
| 5,333,625 A | 8/1994 | Klein |
| 5,334,204 A | 8/1994 | Clewett et al. |
| 5,336,229 A | 8/1994 | Noda |
| 5,336,231 A | 8/1994 | Adair |
| 5,336,240 A | 8/1994 | Metzler et al. |
| 5,339,870 A | 8/1994 | Green et al. |
| 5,342,369 A | 8/1994 | Harryman, II |
| 5,346,462 A | 9/1994 | Barber |
| 5,354,298 A | 10/1994 | Lee et al. |
| 5,356,412 A | 10/1994 | Golds et al. |
| 5,356,413 A | 10/1994 | Martins et al. |
| 5,356,417 A | 10/1994 | Golds |
| 5,358,511 A | 10/1994 | Gatturna et al. |
| 5,360,431 A | 11/1994 | Puno et al. |
| 5,362,294 A | 11/1994 | Seitzinger |
| 5,364,400 A | 11/1994 | Rego, Jr. et al. |
| 5,366,461 A | 11/1994 | Blasnik |
| 5,368,599 A | 11/1994 | Hirsch et al. |
| 5,370,661 A | 12/1994 | Branch |
| 5,370,662 A | 12/1994 | Stone et al. |
| 5,372,146 A | 12/1994 | Branch |
| 5,372,604 A | 12/1994 | Trott |
| 5,372,821 A | 12/1994 | Badylak et al. |
| 5,374,268 A | 12/1994 | Sander |
| 5,379,492 A | 1/1995 | Glesser |
| 5,383,878 A | 1/1995 | Roger et al. |
| 5,383,904 A | 1/1995 | Totakura et al. |
| 5,391,171 A | 2/1995 | Schmieding |

| Patent | Date | Name |
|---|---|---|
| 5,391,176 A | 2/1995 | de la Torre |
| 5,391,182 A | 2/1995 | Chin |
| 5,393,302 A | 2/1995 | Clark et al. |
| RE34,871 E | 3/1995 | McGuire et al. |
| 5,397,356 A | 3/1995 | Goble et al. |
| 5,403,328 A | 4/1995 | Shallman |
| 5,403,329 A | 4/1995 | Hinchcliffe |
| 5,403,348 A | 4/1995 | Bonutti |
| 5,405,359 A | 4/1995 | Pierce |
| 5,417,691 A | 5/1995 | Hayhurst |
| 5,417,698 A | 5/1995 | Green et al. |
| 5,417,712 A | 5/1995 | Whittaker et al. |
| 5,423,819 A | 6/1995 | Small et al. |
| 5,423,821 A | 6/1995 | Pasque |
| 5,423,823 A | 6/1995 | Schmieding |
| 5,423,860 A | 6/1995 | Lizardi et al. |
| 5,425,733 A | 6/1995 | Schmieding |
| 5,425,766 A | 6/1995 | Bowald |
| 5,433,751 A | 7/1995 | Christel et al. |
| 5,437,680 A | 8/1995 | Yoon |
| 5,437,685 A | 8/1995 | Blasnik |
| 5,439,684 A | 8/1995 | Prewett et al. |
| 5,441,508 A | 8/1995 | Gazielly et al. |
| 5,443,468 A | 8/1995 | Johnson |
| 5,443,482 A | 8/1995 | Stone et al. |
| 5,443,483 A | 8/1995 | Kirsch |
| 5,443,509 A | 8/1995 | Boucher et al. |
| 5,445,833 A | 8/1995 | Badylak et al. |
| 5,447,512 A | 9/1995 | Wilson et al. |
| 5,449,361 A | 9/1995 | Preissman |
| 5,451,203 A | 9/1995 | Lamb |
| 5,454,811 A | 10/1995 | Huebner |
| 5,454,821 A | 10/1995 | Harm et al. |
| 5,456,685 A | 10/1995 | Huebner |
| 5,456,722 A | 10/1995 | McLeod et al. |
| 5,458,601 A | 10/1995 | Young, Jr. et al. |
| 5,458,604 A | 10/1995 | Schmieding |
| 5,462,542 A | 10/1995 | Alesi, Jr. |
| 5,462,560 A | 10/1995 | Stevens |
| 5,464,426 A | 11/1995 | Bonutti |
| 5,464,427 A | 11/1995 | Curtis et al. |
| 5,464,440 A | 11/1995 | Johansson |
| 5,466,237 A | 11/1995 | Byrd, III et al. |
| 5,467,786 A | 11/1995 | Allen et al. |
| 5,470,334 A | 11/1995 | Ross et al. |
| 5,470,337 A | 11/1995 | Moss |
| 5,470,338 A | 11/1995 | Whitfield et al. |
| 5,472,452 A | 12/1995 | Trott |
| 5,474,565 A | 12/1995 | Trott |
| 5,474,568 A | 12/1995 | Scott |
| 5,474,572 A | 12/1995 | Hayhurst |
| 5,478,344 A | 12/1995 | Stone et al. |
| 5,478,345 A | 12/1995 | Stone et al. |
| 5,480,403 A | 1/1996 | Lee et al. |
| 5,480,406 A | 1/1996 | Nolan et al. |
| 5,484,442 A | 1/1996 | Melker et al. |
| 5,486,197 A | 1/1996 | Le et al. |
| 5,490,750 A | 2/1996 | Gundy |
| 5,496,331 A | 3/1996 | Xu et al. |
| 5,496,348 A | 3/1996 | Bonutti |
| 5,500,000 A | 3/1996 | Feagin et al. |
| 5,505,736 A | 4/1996 | Reimels et al. |
| 5,507,754 A | 4/1996 | Green et al. |
| 5,520,691 A | 5/1996 | Branch |
| 5,520,700 A | 5/1996 | Beyar et al. |
| 5,520,702 A | 5/1996 | Sauer et al. |
| 5,522,817 A | 6/1996 | Sander et al. |
| 5,522,820 A | 6/1996 | Caspari et al. |
| 5,522,844 A | 6/1996 | Johnson |
| 5,522,845 A | 6/1996 | Wenstrom, Jr. |
| 5,522,846 A | 6/1996 | Bonutti |
| 5,524,946 A | 6/1996 | Thompson |
| 5,527,321 A | 6/1996 | Hinchliffe |
| 5,527,342 A | 6/1996 | Pietrzak et al. |
| 5,527,343 A | 6/1996 | Bonutti |
| 5,531,759 A | 7/1996 | Kensey et al. |
| 5,534,012 A | 7/1996 | Bonutti |
| 5,536,270 A | 7/1996 | Songer et al. |
| 5,540,698 A | 7/1996 | Preissman |
| 5,540,703 A | 7/1996 | Barker, Jr. et al. |
| 5,540,718 A | 7/1996 | Bartlett |
| 5,545,168 A | 8/1996 | Burke |
| 5,545,178 A | 8/1996 | Kensey et al. |
| 5,545,180 A | 8/1996 | Le et al. |
| 5,545,228 A | 8/1996 | Kambin |
| 5,549,613 A | 8/1996 | Goble et al. |
| 5,549,617 A | 8/1996 | Green et al. |
| 5,549,619 A | 8/1996 | Peters et al. |
| 5,549,630 A | 8/1996 | Bonutti |
| 5,549,631 A | 8/1996 | Bonutti |
| 5,562,683 A | 10/1996 | Chan |
| 5,562,685 A | 10/1996 | Mollenauer et al. |
| 5,562,686 A | 10/1996 | Sauer et al. |
| 5,569,269 A | 10/1996 | Hart et al. |
| 5,569,305 A | 10/1996 | Bonutti |
| 5,571,090 A | 11/1996 | Sherts |
| 5,571,139 A | 11/1996 | Jenkins, Jr. |
| 5,572,655 A | 11/1996 | Tuljapurkar et al. |
| 5,573,286 A | 11/1996 | Rogozinski |
| 5,573,542 A | 11/1996 | Stevens |
| 5,573,548 A | 11/1996 | Nazre et al. |
| 5,577,299 A | 11/1996 | Thompson et al. |
| 5,578,057 A | 11/1996 | Wenstrom, Jr. |
| 5,584,695 A | 12/1996 | Lal Sachdeva et al. |
| 5,584,835 A | 12/1996 | Greenfield |
| 5,584,836 A | 12/1996 | Ballintyn et al. |
| 5,584,862 A | 12/1996 | Bonutti |
| 5,586,986 A | 12/1996 | Hinchliffe |
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,618,290 A | 4/1997 | Toy et al. |
| 5,626,611 A | 5/1997 | Liu et al. |
| 5,626,614 A | 5/1997 | Hart |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle |
| 5,643,295 A | 7/1997 | Yoon |
| 5,643,319 A | 7/1997 | Green et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,959 A | 7/1997 | Hannam et al. |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,662,681 A | 9/1997 | Nash et al. |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,334 A | 10/1997 | Evans et al. |
| 5,681,352 A | 10/1997 | Clancy, III et al. |
| 5,683,419 A | 11/1997 | Thal |
| 5,688,285 A | 11/1997 | Yamada et al. |
| 5,690,676 A | 11/1997 | DiPoto et al. |
| 5,690,678 A | 11/1997 | Johnson |
| 5,693,046 A | 12/1997 | Songer et al. |

| | | | | | |
|---|---|---|---|---|---|
| 5,695,497 A | 12/1997 | Stahelin et al. | 5,868,740 A | 2/1999 | LeVeen et al. |
| 5,697,929 A | 12/1997 | Mellinger | 5,868,748 A | 2/1999 | Burke |
| 5,699,657 A | 12/1997 | Paulson | 5,868,789 A | 2/1999 | Huebner |
| 5,702,397 A | 12/1997 | Goble et al. | 5,871,484 A | 2/1999 | Spievack et al. |
| 5,702,422 A | 12/1997 | Stone | 5,871,486 A | 2/1999 | Huebner et al. |
| 5,702,462 A | 12/1997 | Oberlander | 5,871,490 A | 2/1999 | Schulze et al. |
| 5,707,373 A | 1/1998 | Sevrain et al. | 5,885,294 A | 3/1999 | Pedlick et al. |
| 5,711,969 A | 1/1998 | Patel et al. | 5,891,168 A | 4/1999 | Thal |
| 5,713,005 A | 1/1998 | Proebsting | 5,893,592 A | 4/1999 | Schulze et al. |
| 5,713,904 A | 2/1998 | Errico et al. | 5,895,395 A | 4/1999 | Yeung |
| 5,713,905 A | 2/1998 | Goble et al. | 5,897,564 A | 4/1999 | Schulze et al. |
| 5,713,921 A | 2/1998 | Bonutti | 5,897,574 A | 4/1999 | Bonutti |
| 5,716,359 A | 2/1998 | Ojima et al. | 5,899,902 A | 5/1999 | Brown et al. |
| 5,716,397 A | 2/1998 | Myers | 5,899,938 A | 5/1999 | Sklar et al. |
| 5,718,717 A | 2/1998 | Bonutti | 5,908,421 A | 6/1999 | Beger |
| 5,720,747 A | 2/1998 | Burke | 5,908,436 A | 6/1999 | Cuschieri et al. |
| 5,720,765 A | 2/1998 | Thal | 5,910,148 A | 6/1999 | Reimels et al. |
| 5,720,766 A | 2/1998 | Zang et al. | 5,911,721 A | 6/1999 | Nicholson et al. |
| 5,722,976 A | 3/1998 | Brown | 5,918,604 A | 7/1999 | Whelan |
| 5,725,529 A | 3/1998 | Nicholson et al. | 5,921,986 A | 7/1999 | Bonutti |
| 5,725,549 A | 3/1998 | Lam | 5,925,008 A | 7/1999 | Douglas |
| 5,725,556 A | 3/1998 | Moser et al. | 5,928,231 A | 7/1999 | Klein et al. |
| 5,725,581 A | 3/1998 | Br.ang.nemark | 5,928,267 A | 7/1999 | Bonutti et al. |
| 5,725,582 A | 3/1998 | Bevan et al. | RE36,289 E | 8/1999 | Le et al. |
| 5,726,722 A | 3/1998 | Uehara et al. | 5,931,838 A | 8/1999 | Vito |
| 5,728,107 A | 3/1998 | Zlock et al. | 5,931,844 A | 8/1999 | Thompson et al. |
| 5,728,109 A | 3/1998 | Schulze et al. | 5,931,869 A | 8/1999 | Boucher et al. |
| 5,728,136 A | 3/1998 | Thal | 5,935,119 A | 8/1999 | Guy et al. |
| 5,733,293 A | 3/1998 | Scirica et al. | 5,935,133 A | 8/1999 | Wagner et al. |
| 5,733,306 A | 3/1998 | Bonutti | 5,935,149 A | 8/1999 | Ek |
| 5,733,307 A | 3/1998 | Dinsdale | 5,938,668 A | 8/1999 | Scirica et al. |
| 5,735,875 A | 4/1998 | Bonutti et al. | 5,941,439 A | 8/1999 | Kammerer et al. |
| 5,741,259 A | 4/1998 | Chan | 5,941,900 A | 8/1999 | Bonutti |
| 5,741,260 A | 4/1998 | Songer et al. | 5,944,739 A | 8/1999 | Zlock et al. |
| 5,741,281 A | 4/1998 | Martin | 5,946,783 A | 9/1999 | Plociennik et al. |
| 5,743,912 A | 4/1998 | Lahille et al. | 5,947,915 A | 9/1999 | Thibodo, Jr. |
| 5,746,751 A | 5/1998 | Sherts | 5,947,982 A | 9/1999 | Duran |
| 5,746,752 A | 5/1998 | Burkhart | 5,947,999 A | 9/1999 | Groiso |
| 5,746,754 A | 5/1998 | Chan | 5,948,002 A | 9/1999 | Bonutti |
| 5,749,898 A | 5/1998 | Schulze et al. | 5,951,559 A | 9/1999 | Burkhart |
| 5,755,729 A | 5/1998 | de la Torre et al. | 5,951,560 A | 9/1999 | Simon et al. |
| 5,755,791 A | 5/1998 | Whitson et al. | 5,954,747 A | 9/1999 | Clark |
| 5,766,176 A | 6/1998 | Duncan | 5,957,953 A | 9/1999 | DiPoto et al. |
| 5,766,218 A | 6/1998 | Arnott | 5,961,521 A | 10/1999 | Roger |
| 5,766,250 A | 6/1998 | Chervitz et al. | 5,961,524 A | 10/1999 | Crombie |
| 5,769,894 A | 6/1998 | Ferragamo | 5,964,764 A | 10/1999 | West, Jr. et al. |
| 5,769,899 A | 6/1998 | Schwartz et al. | 5,964,767 A | 10/1999 | Tapia et al. |
| 5,772,673 A | 6/1998 | Cuny et al. | 5,964,769 A | 10/1999 | Wagner et al. |
| 5,776,196 A | 7/1998 | Matsuzaki et al. | 5,964,783 A | 10/1999 | Grafton et al. |
| 5,782,845 A | 7/1998 | Shewchuk | 5,968,045 A | 10/1999 | Frazier |
| 5,782,862 A | 7/1998 | Bonutti | 5,968,047 A | 10/1999 | Reed |
| 5,782,864 A | 7/1998 | Lizardi | 5,968,077 A | 10/1999 | Wojciechowicz et al. |
| 5,782,866 A | 7/1998 | Wenstrom, Jr. | 5,970,697 A | 10/1999 | Jacobs et al. |
| 5,785,714 A | 7/1998 | Morgan et al. | 5,972,006 A | 10/1999 | Sciaino, Jr. |
| 5,792,142 A | 8/1998 | Galitzer | 5,976,125 A | 11/1999 | Graham |
| 5,792,149 A | 8/1998 | Sherts et al. | 5,976,127 A | 11/1999 | Lax |
| 5,796,127 A | 8/1998 | Hayafuji et al. | 5,980,524 A | 11/1999 | Justin et al. |
| 5,797,915 A | 8/1998 | Pierson, III et al. | 5,980,539 A | 11/1999 | Kontos |
| 5,797,916 A | 8/1998 | McDowell | 5,980,558 A | 11/1999 | Wiley |
| 5,797,928 A | 8/1998 | Kogasaka | 5,980,559 A | 11/1999 | Bonutti |
| 5,800,407 A | 9/1998 | Eldor | 5,989,252 A | 11/1999 | Fumex |
| 5,810,824 A | 9/1998 | Chan | 5,989,256 A | 11/1999 | Kuslich et al. |
| 5,810,848 A | 9/1998 | Hayhurst | 5,989,282 A | 11/1999 | Bonutti |
| 5,814,056 A | 9/1998 | Prosst et al. | 5,993,452 A | 11/1999 | Vandewalle |
| 5,814,069 A | 9/1998 | Schulze et al. | 5,993,476 A | 11/1999 | Groiso |
| 5,814,070 A | 9/1998 | Borzone et al. | 5,997,542 A | 12/1999 | Burke |
| 5,814,072 A | 9/1998 | Bonutti | 5,997,552 A | 12/1999 | Person et al. |
| 5,814,073 A | 9/1998 | Bonutti | 5,997,575 A | 12/1999 | Whitson et al. |
| 5,823,980 A | 10/1998 | Kopfer | 6,001,100 A | 12/1999 | Sherman et al. |
| 5,824,011 A | 10/1998 | Stone et al. | 6,007,538 A | 12/1999 | Levin |
| 5,824,066 A | 10/1998 | Gross | 6,007,567 A | 12/1999 | Bonutti |
| 5,830,234 A | 11/1998 | Wojciechowicz et al. | 6,010,525 A | 1/2000 | Bonutti et al. |
| 5,843,084 A | 12/1998 | Hart et al. | 6,016,727 A | 1/2000 | Morgan |
| 5,845,645 A | 12/1998 | Bonutti | 6,022,352 A | 2/2000 | Vandewalle |
| 5,846,254 A | 12/1998 | Schulze et al. | 6,022,373 A | 2/2000 | Li |
| 5,848,983 A | 12/1998 | Basaj et al. | 6,024,758 A | 2/2000 | Thal |
| 5,849,012 A | 12/1998 | Abboudi | 6,027,523 A | 2/2000 | Schmieding |
| 5,860,973 A | 1/1999 | Michelson | 6,030,410 A | 2/2000 | Zurbrugg |
| 5,860,978 A | 1/1999 | McDevitt et al. | 6,033,429 A | 3/2000 | Magovern |

| Patent Number | Date | Inventor |
|---|---|---|
| 6,033,430 A | 3/2000 | Bonutti |
| 6,039,753 A | 3/2000 | Meislin |
| 6,041,485 A | 3/2000 | Pedlick et al. |
| 6,042,601 A | 3/2000 | Smith |
| 6,045,551 A | 4/2000 | Bonutti |
| 6,045,571 A | 4/2000 | Hill et al. |
| 6,045,572 A | 4/2000 | Johnson et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,051,007 A | 4/2000 | Hogendijk et al. |
| 6,053,916 A | 4/2000 | Moore |
| 6,053,921 A | 4/2000 | Wagner et al. |
| 6,056,752 A | 5/2000 | Roger |
| 6,056,772 A | 5/2000 | Bonutti |
| 6,056,773 A | 5/2000 | Bonutti |
| 6,059,817 A | 5/2000 | Bonutti et al. |
| 6,059,818 A | 5/2000 | Johnson et al. |
| 6,062,344 A | 5/2000 | Okabe et al. |
| 6,068,648 A | 5/2000 | Cole et al. |
| 6,071,305 A | 6/2000 | Brown et al. |
| 6,074,403 A | 6/2000 | Nord |
| 6,077,277 A | 6/2000 | Mollenauer et al. |
| 6,077,292 A | 6/2000 | Bonutti |
| 6,080,185 A | 6/2000 | Johnson et al. |
| 6,086,591 A | 7/2000 | Bojarski |
| 6,086,592 A | 7/2000 | Rosenberg et al. |
| 6,086,608 A | 7/2000 | Ek et al. |
| 6,093,200 A | 7/2000 | Liu et al. |
| 6,096,060 A | 8/2000 | Fitts et al. |
| 6,099,527 A | 8/2000 | Hochschuler et al. |
| 6,099,530 A | 8/2000 | Simonian et al. |
| 6,099,568 A | 8/2000 | Simonian et al. |
| 6,106,545 A | 8/2000 | Egan |
| 6,110,128 A | 8/2000 | Andelin et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,179,840 B1 | 1/2001 | Bowman |
| 6,183,461 B1 | 2/2001 | Matsuura et al. |
| 6,187,025 B1 | 2/2001 | Machek |
| 6,190,401 B1 | 2/2001 | Green et al. |
| 6,190,411 B1 | 2/2001 | Lo |
| 6,193,754 B1 | 2/2001 | Seedhom |
| 6,200,318 B1 | 3/2001 | Har-Shai et al. |
| 6,200,329 B1 | 3/2001 | Fung et al. |
| 6,200,330 B1 | 3/2001 | Benderev et al. |
| 6,203,556 B1 | 3/2001 | Evans et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,012 B1 | 4/2001 | Karpman et al. |
| 6,217,580 B1 | 4/2001 | Levin |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,280,474 B1 | 8/2001 | Cassidy et al. |
| 6,283,973 B1 | 9/2001 | Hubbard et al. |
| 6,283,996 B1 | 9/2001 | Chervitz et al. |
| 6,287,307 B1 | 9/2001 | Abboudi |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,302,899 B1 | 10/2001 | Johnson et al. |
| 6,306,156 B1 | 10/2001 | Clark |
| 6,306,159 B1 | 10/2001 | Schwartz et al. |
| 6,309,405 B1 | 10/2001 | Bonutti |
| 6,312,448 B1 | 11/2001 | Bonutti |
| 6,315,788 B1 | 11/2001 | Roby |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,358,270 B1 | 3/2002 | Lemer |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,391,030 B1 | 5/2002 | Wagner et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,123 B1 | 8/2002 | Magovern |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,482,210 B1 | 11/2002 | Skiba et al. |
| 6,485,504 B1 | 11/2002 | Johnson et al. |
| 6,491,714 B1 | 12/2002 | Bennett |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,506,190 B1 | 1/2003 | Walshe |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,578 B2 | 2/2003 | Hein |
| 6,517,579 B1 | 2/2003 | Paulos et al. |

| Patent | Date | Inventor |
|---|---|---|
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,769 B1 | 4/2003 | Miller, III |
| 6,540,770 B1 | 4/2003 | Tornier et al. |
| 6,544,281 B2 | 4/2003 | ElAttrache et al. |
| 6,547,564 B1 | 4/2003 | Hansson |
| 6,547,778 B1 | 4/2003 | Sklar et al. |
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob |
| 6,554,830 B1 | 4/2003 | Chappius |
| 6,554,852 B1 | 4/2003 | Oberlander |
| 6,554,862 B2 | 4/2003 | Hays et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,599,319 B2 | 7/2003 | Knudsen et al. |
| 6,605,096 B1 | 8/2003 | Ritchart |
| 6,607,548 B2 | 8/2003 | Pohjonen et al. |
| 6,610,079 B1 | 8/2003 | Li et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,638,312 B2 | 10/2003 | Plouhar et al. |
| 6,641,596 B1 | 11/2003 | Lizardi |
| 6,641,597 B2 | 11/2003 | Dreyfuss et al. |
| 6,645,227 B2 | 11/2003 | Fallin et al. |
| 6,648,921 B2 | 11/2003 | Anderson et al. |
| 6,652,450 B2 | 11/2003 | Neisz et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,666,877 B2 | 12/2003 | Morgan et al. |
| 6,682,533 B1 | 1/2004 | Dinsdale et al. |
| 6,682,549 B2 | 1/2004 | Bartlett |
| 6,685,728 B2 | 2/2004 | Sinnott et al. |
| 6,689,137 B2 | 2/2004 | Reed |
| 6,689,153 B1 | 2/2004 | Skiba |
| 6,689,154 B2 | 2/2004 | Bartlett |
| 6,692,499 B2 | 2/2004 | Tormala et al. |
| 6,692,516 B2 | 2/2004 | West, Jr. et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,737,053 B1 | 5/2004 | Goh et al. |
| 6,746,483 B1 | 6/2004 | Bojarski et al. |
| 6,752,810 B1 | 6/2004 | Gao et al. |
| 6,752,831 B2 | 6/2004 | Sybert et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,779,701 B2 | 8/2004 | Bailly et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,860,895 B1 | 3/2005 | Akerfeldt et al. |
| 6,863,671 B1 | 3/2005 | Strobel et al. |
| 6,872,040 B2 | 3/2005 | Deeg et al. |
| 6,872,210 B2 | 3/2005 | Hearn |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,905,513 B1 | 6/2005 | Metzger |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,966,887 B1 | 11/2005 | Chin |
| 6,966,916 B2 | 11/2005 | Kumar |
| 6,969,391 B1 | 11/2005 | Gazzani |
| 6,969,398 B2 | 11/2005 | Stevens et al. |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 7,001,429 B2 | 2/2006 | Ferguson |
| 7,004,959 B2 | 2/2006 | Bonutti |
| 7,048,754 B2 | 5/2006 | Martin et al. |
| 7,052,499 B2 | 5/2006 | Steger et al. |
| 7,066,942 B2 | 6/2006 | Treace |
| 7,066,944 B2 | 6/2006 | Laufer et al. |
| 7,081,126 B2 | 7/2006 | McDevitt et al. |
| 7,087,064 B1 | 8/2006 | Hyde |
| 7,105,010 B2 | 9/2006 | Hart et al. |
| 7,112,221 B2 | 9/2006 | Harris |
| 7,118,583 B2 | 10/2006 | O'Quinn et al. |
| 7,125,421 B2 | 10/2006 | Tremulis et al. |
| 7,131,467 B2 | 11/2006 | Gao et al. |
| 7,137,996 B2 | 11/2006 | Steiner et al. |
| 7,141,066 B2 | 11/2006 | Steiner et al. |
| 7,144,414 B2 | 12/2006 | Harvie et al. |
| 7,153,127 B2 | 12/2006 | Struble et al. |
| 7,153,307 B2 | 12/2006 | Scribner et al. |
| 7,153,312 B1 | 12/2006 | Torrie et al. |
| 7,153,327 B1 | 12/2006 | Metzger |
| 7,160,333 B2 | 1/2007 | Plouhar et al. |

| | | |
|---|---|---|
| 7,201,722 B2 | 4/2007 | Krueger |
| 7,255,675 B2 | 8/2007 | Gertner et al. |
| 7,255,715 B2 * | 8/2007 | Metzger ............... 623/20.17 |
| 7,261,716 B2 | 8/2007 | Strobel et al. |
| 7,264,634 B2 | 9/2007 | Schmieding |
| 7,285,124 B2 | 10/2007 | Foerster |
| 7,303,577 B1 | 12/2007 | Dean |
| 7,306,417 B2 | 12/2007 | Dorstewitz |
| 7,326,222 B2 | 2/2008 | Dreyfuss et al. |
| 7,329,272 B2 | 2/2008 | Burkhart et al. |
| 7,361,179 B2 | 4/2008 | Rousseau et al. |
| 7,377,845 B2 | 5/2008 | Stewart et al. |
| 7,390,329 B2 | 6/2008 | Westra et al. |
| 7,390,332 B2 | 6/2008 | Selvitelli et al. |
| 7,399,018 B1 | 7/2008 | Khachaturian |
| 7,442,210 B2 | 10/2008 | Segal et al. |
| 7,465,308 B2 | 12/2008 | Sikora et al. |
| 7,494,506 B2 | 2/2009 | Brulez et al. |
| 7,513,910 B2 | 4/2009 | Buskirk et al. |
| 7,578,825 B2 | 8/2009 | Huebner |
| 7,585,311 B2 | 9/2009 | Green et al. |
| 7,597,705 B2 | 10/2009 | Forsberg et al. |
| 7,601,165 B2 | 10/2009 | Stone |
| 7,608,092 B1 | 10/2009 | Schaffhausen |
| 7,608,098 B1 | 10/2009 | Stone et al. |
| 7,615,076 B2 | 11/2009 | Cauthen, III et al. |
| 7,621,937 B2 | 11/2009 | Pipenhagen et al. |
| 7,632,287 B2 | 12/2009 | Baker et al. |
| 7,651,509 B2 | 1/2010 | Bojarski et al. |
| 7,658,750 B2 | 2/2010 | Li |
| 7,658,751 B2 | 2/2010 | Stone et al. |
| 7,670,279 B2 | 3/2010 | Gertner |
| 7,678,123 B2 | 3/2010 | Chanduszko |
| 7,695,493 B2 | 4/2010 | Saadat et al. |
| 7,731,732 B2 | 6/2010 | Ken |
| 7,736,379 B2 | 6/2010 | Ewers et al. |
| 7,749,250 B2 | 7/2010 | Stone et al. |
| 7,758,594 B2 | 7/2010 | Lamson et al. |
| 7,758,611 B2 | 7/2010 | Kato |
| 7,776,041 B1 | 8/2010 | Walters |
| 7,819,895 B2 | 10/2010 | Ginn et al. |
| 7,828,850 B2 | 11/2010 | Cauthen, III et al. |
| 7,857,830 B2 | 12/2010 | Stone et al. |
| 7,875,058 B2 | 1/2011 | Holmes, Jr. |
| 7,887,586 B2 * | 2/2011 | Linares ............... 623/13.11 |
| 7,905,903 B2 | 3/2011 | Stone et al. |
| 7,905,904 B2 | 3/2011 | Stone et al. |
| 7,909,851 B2 | 3/2011 | Stone et al. |
| 7,938,847 B2 | 5/2011 | Fanton et al. |
| 7,959,650 B2 | 6/2011 | Kaiser et al. |
| 7,981,140 B2 | 7/2011 | Burkhart |
| 7,998,203 B2 * | 8/2011 | Blum ............... 623/13.12 |
| 8,062,334 B2 | 11/2011 | Green et al. |
| 8,075,574 B2 | 12/2011 | May et al. |
| 8,088,130 B2 | 1/2012 | Kaiser et al. |
| 8,114,127 B2 | 2/2012 | West, Jr. |
| 8,114,128 B2 | 2/2012 | Cauldwell et al. |
| 8,118,835 B2 | 2/2012 | Weisel et al. |
| 8,118,836 B2 | 2/2012 | Denham et al. |
| 8,128,658 B2 | 3/2012 | Kaiser et al. |
| 8,137,382 B2 | 3/2012 | Denham et al. |
| 8,167,906 B2 | 5/2012 | Cauldwell et al. |
| 8,221,454 B2 | 7/2012 | Schaffhausen |
| 8,231,654 B2 | 7/2012 | Kaiser et al. |
| 8,251,998 B2 | 8/2012 | Hoeppner et al. |
| 8,252,022 B2 | 8/2012 | Holman et al. |
| 2001/0010005 A1 | 7/2001 | Kammerer et al. |
| 2001/0014825 A1 | 8/2001 | Burke et al. |
| 2001/0019649 A1 | 9/2001 | Field et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013607 A1 | 1/2002 | Lemer |
| 2002/0013608 A1 | 1/2002 | ElAttrache et al. |
| 2002/0019649 A1 | 2/2002 | Sikora et al. |
| 2002/0029066 A1 | 3/2002 | Foerster |
| 2002/0032465 A1 | 3/2002 | Lemer |
| 2002/0055780 A1 | 5/2002 | Sklar |
| 2002/0058966 A1 | 5/2002 | Tormala et al. |
| 2002/0077659 A1 | 6/2002 | Johnson et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128654 A1 | 9/2002 | Steger et al. |
| 2002/0128684 A1 | 9/2002 | Foerster |
| 2002/0129820 A1 | 9/2002 | Ryan et al. |
| 2002/0143336 A1 | 10/2002 | Hearn |
| 2002/0147463 A1 | 10/2002 | Martinek |
| 2002/0161401 A1 | 10/2002 | Steiner |
| 2002/0161439 A1 | 10/2002 | Strobel et al. |
| 2002/0165548 A1 | 11/2002 | Jutley |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |
| 2002/0193830 A1 | 12/2002 | Bonutti |
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078585 A1 | 4/2003 | Johnson et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0083694 A1 | 5/2003 | Miller |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0105489 A1 | 6/2003 | Eichhorn et al. |
| 2003/0120309 A1 | 6/2003 | Colleran et al. |
| 2003/0130694 A1 | 7/2003 | Bojarski et al. |
| 2003/0130695 A1 | 7/2003 | McDevitt et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0153947 A1 | 8/2003 | Koseki |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0195564 A1 | 10/2003 | Tran et al. |
| 2003/0208210 A1 | 11/2003 | Dreyfuss et al. |
| 2003/0212456 A1 | 11/2003 | Lipchitz et al. |
| 2003/0220660 A1 | 11/2003 | Kortenbach et al. |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0024457 A1 | 2/2004 | Boyce et al. |
| 2004/0044391 A1 | 3/2004 | Porter |
| 2004/0059357 A1 | 3/2004 | Koseki |
| 2004/0087981 A1 | 5/2004 | Berube et al. |
| 2004/0092936 A1 | 5/2004 | Miller et al. |
| 2004/0093032 A1 | 5/2004 | Sinnott et al. |
| 2004/0098051 A1 | 5/2004 | Fallin et al. |

| | | |
|---|---|---|
| 2004/0098053 A1 | 5/2004 | Tran |
| 2004/0111117 A1 | 6/2004 | Colleran et al. |
| 2004/0122431 A1 | 6/2004 | Biedermann et al. |
| 2004/0133206 A1 | 7/2004 | Stevens et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0138747 A1 | 7/2004 | Kaladelfos |
| 2004/0143344 A1 | 7/2004 | Malaviya et al. |
| 2004/0147932 A1 | 7/2004 | Burkinshaw et al. |
| 2004/0147958 A1 | 7/2004 | Lam et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0187314 A1 | 9/2004 | Johnson |
| 2004/0199169 A1 | 10/2004 | Koons et al. |
| 2004/0204722 A1 | 10/2004 | Sikora et al. |
| 2004/0220574 A1 | 11/2004 | Pelo et al. |
| 2004/0225292 A1 | 11/2004 | Sasso et al. |
| 2004/0225305 A1 | 11/2004 | Ewers et al. |
| 2004/0236353 A1 | 11/2004 | Bain et al. |
| 2004/0236373 A1 | 11/2004 | Anspach |
| 2004/0243139 A1 | 12/2004 | Lewis et al. |
| 2004/0243178 A1 | 12/2004 | Haut et al. |
| 2004/0243235 A1 | 12/2004 | Goh et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267286 A1 | 12/2004 | Gao et al. |
| 2004/0267304 A1 | 12/2004 | Zannis et al. |
| 2004/0267309 A1 | 12/2004 | Garvin |
| 2005/0021087 A1 | 1/2005 | Koseki |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0055037 A1 | 3/2005 | Fathauer |
| 2005/0064042 A1 | 3/2005 | Vunjak-Novakovic et al. |
| 2005/0065521 A1 | 3/2005 | Steger et al. |
| 2005/0070928 A1 | 3/2005 | Heino et al. |
| 2005/0074495 A1 | 4/2005 | Schwartz et al. |
| 2005/0085819 A1 | 4/2005 | Ellis et al. |
| 2005/0090828 A1 | 4/2005 | Alford |
| 2005/0090862 A1 | 4/2005 | McDevitt et al. |
| 2005/0096696 A1 | 5/2005 | Forsberg |
| 2005/0096697 A1 | 5/2005 | Forsberg et al. |
| 2005/0096743 A1 | 5/2005 | Schmieding et al. |
| 2005/0101957 A1 | 5/2005 | Buskirk et al. |
| 2005/0107795 A1 | 5/2005 | Morris et al. |
| 2005/0107828 A1 | 5/2005 | Reese |
| 2005/0119531 A1 | 6/2005 | Sharratt |
| 2005/0119696 A1 | 6/2005 | Walters et al. |
| 2005/0124996 A1 | 6/2005 | Hearn |
| 2005/0125031 A1 | 6/2005 | Pipenhagen et al. |
| 2005/0125036 A1 | 6/2005 | Roby |
| 2005/0125073 A1 | 6/2005 | Orban et al. |
| 2005/0131413 A1 | 6/2005 | O'Driscoll et al. |
| 2005/0137600 A1 | 6/2005 | Jacobs et al. |
| 2005/0137624 A1 | 6/2005 | Fallman |
| 2005/0149033 A1 | 7/2005 | McGuire et al. |
| 2005/0149122 A1 | 7/2005 | McDevitt et al. |
| 2005/0149187 A1 | 7/2005 | Clark et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0187565 A1 | 8/2005 | Baker et al. |
| 2005/0187577 A1 | 8/2005 | Selvitelli et al. |
| 2005/0187635 A1 | 8/2005 | Metzger |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0240198 A1 | 10/2005 | Albertson et al. |
| 2005/0251159 A1 | 11/2005 | Ewers et al. |
| 2005/0251177 A1 | 11/2005 | Saadat et al. |
| 2005/0251208 A1 | 11/2005 | Elmer et al. |
| 2005/0251210 A1 | 11/2005 | Westra et al. |
| 2005/0267479 A1 | 12/2005 | Morgan et al. |
| 2005/0267533 A1 | 12/2005 | Gertner |
| 2005/0277939 A1 | 12/2005 | Miller |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0004410 A1 | 1/2006 | Nobis et al. |
| 2006/0015103 A1 | 1/2006 | Burke |
| 2006/0015106 A1 | 1/2006 | Lerch et al. |
| 2006/0030884 A1 | 2/2006 | Yeung et al. |
| 2006/0030948 A1 | 2/2006 | Manrique et al. |
| 2006/0036265 A1 | 2/2006 | Dant |
| 2006/0052818 A1 | 3/2006 | Drake et al. |
| 2006/0064125 A1 | 3/2006 | Henderson et al. |
| 2006/0064126 A1 | 3/2006 | Fallin et al. |
| 2006/0069334 A1 | 3/2006 | Moskowitz |
| 2006/0079904 A1 | 4/2006 | Thal |
| 2006/0084943 A1 | 4/2006 | Rosenman et al. |
| 2006/0085000 A1 | 4/2006 | Mohr et al. |
| 2006/0089672 A1 | 4/2006 | Martinek |
| 2006/0100627 A1 | 5/2006 | Stone et al. |
| 2006/0100637 A1 | 5/2006 | Rathbun et al. |
| 2006/0106423 A1 | 5/2006 | Weisel et al. |
| 2006/0111721 A1 | 5/2006 | Puricelli et al. |
| 2006/0116685 A1 | 6/2006 | Urbanski et al. |
| 2006/0121084 A1 | 6/2006 | Borden et al. |
| 2006/0122611 A1 | 6/2006 | Morales et al. |
| 2006/0135958 A1 | 6/2006 | Marissen et al. |
| 2006/0149266 A1 | 7/2006 | Cordasco |
| 2006/0161161 A1 | 7/2006 | Shifrin et al. |
| 2006/0167458 A1 | 7/2006 | Gabele |
| 2006/0167481 A1 | 7/2006 | Baker et al. |
| 2006/0167482 A1 | 7/2006 | Swain et al. |
| 2006/0173492 A1 | 8/2006 | Akerfeldt et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0195101 A1 | 8/2006 | Stevens |
| 2006/0200235 A1 | 9/2006 | Bianchi et al. |
| 2006/0212055 A1 | 9/2006 | Karabey et al. |
| 2006/0229671 A1 | 10/2006 | Steiner et al. |
| 2006/0235407 A1 | 10/2006 | Wang et al. |
| 2006/0241624 A1 | 10/2006 | Kizuka et al. |
| 2006/0247642 A1 | 11/2006 | Stone et al. |
| 2006/0253130 A1 | 11/2006 | Wolniewicz |
| 2006/0259048 A1 | 11/2006 | Koseki |
| 2006/0271192 A1 | 11/2006 | Olsen et al. |
| 2006/0276793 A1 | 12/2006 | Berry |
| 2006/0276809 A1 | 12/2006 | Oliveira |
| 2006/0276841 A1 | 12/2006 | Barbieri et al. |
| 2006/0280768 A1 | 12/2006 | Hwang et al. |
| 2006/0282082 A1 | 12/2006 | Fanton et al. |
| 2006/0282083 A1 | 12/2006 | Fanton et al. |
| 2006/0282085 A1 | 12/2006 | Stone et al. |
| 2006/0293709 A1 | 12/2006 | Bojarski et al. |
| 2007/0005080 A1 | 1/2007 | Wolniewicz et al. |
| 2007/0010857 A1 | 1/2007 | Sugimoto et al. |
| 2007/0016305 A1 | 1/2007 | Chudik |
| 2007/0021779 A1 | 1/2007 | Garvin et al. |
| 2007/0032800 A1 | 2/2007 | Ortiz et al. |
| 2007/0038218 A1 | 2/2007 | Grevious |
| 2007/0043371 A1 | 2/2007 | Teague et al. |
| 2007/0055249 A1 | 3/2007 | Jensen et al. |
| 2007/0055251 A1 | 3/2007 | Huebner et al. |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0100350 A1 | 5/2007 | Deffenbaugh et al. |

| Publication No. | Date | Inventor |
|---|---|---|
| 2007/0118217 A1 | 5/2007 | Brulez et al. |
| 2007/0123883 A1 | 5/2007 | Ellis et al. |
| 2007/0142838 A1 | 6/2007 | Jordan |
| 2007/0156174 A1 | 7/2007 | Kaiser et al. |
| 2007/0162018 A1 | 7/2007 | Jensen et al. |
| 2007/0185488 A1 | 8/2007 | Pohjonen et al. |
| 2007/0185532 A1 | 8/2007 | Stone et al. |
| 2007/0185568 A1 | 8/2007 | Schwartz |
| 2007/0191849 A1 | 8/2007 | ElAttrache et al. |
| 2007/0191853 A1 | 8/2007 | Stone |
| 2007/0219558 A1 | 9/2007 | Deutsch |
| 2007/0225719 A1 | 9/2007 | Stone et al. |
| 2007/0239209 A1 | 10/2007 | Fallman |
| 2007/0239275 A1 | 10/2007 | Willobee |
| 2007/0250163 A1 | 10/2007 | Cassani |
| 2007/0260251 A1 | 11/2007 | Weier et al. |
| 2007/0260279 A1 | 11/2007 | Hotter et al. |
| 2007/0270856 A1 | 11/2007 | Morales et al. |
| 2007/0276387 A1 | 11/2007 | Morales et al. |
| 2008/0027446 A1 | 1/2008 | Stone et al. |
| 2008/0046009 A1 | 2/2008 | Albertorio et al. |
| 2008/0051836 A1 | 2/2008 | Foerster et al. |
| 2008/0065114 A1 | 3/2008 | Stone et al. |
| 2008/0071299 A1 | 3/2008 | Allinniemi et al. |
| 2008/0082101 A1 | 4/2008 | Reisberg |
| 2008/0082127 A1 | 4/2008 | Stone et al. |
| 2008/0082128 A1 | 4/2008 | Stone |
| 2008/0119892 A1 | 5/2008 | Brailovski et al. |
| 2008/0132753 A1 | 6/2008 | Goddard |
| 2008/0132932 A1 | 6/2008 | Hoeppner et al. |
| 2008/0132948 A1 | 6/2008 | Surti et al. |
| 2008/0140092 A1 | 6/2008 | Stone et al. |
| 2008/0140093 A1 | 6/2008 | Stone et al. |
| 2008/0140128 A1 | 6/2008 | Smisson et al. |
| 2008/0161852 A1 | 7/2008 | Kaiser et al. |
| 2008/0161861 A1 | 7/2008 | Huebner |
| 2008/0172097 A1 | 7/2008 | Lerch et al. |
| 2008/0188933 A1 | 8/2008 | Koob et al. |
| 2008/0188936 A1 | 8/2008 | Ball et al. |
| 2008/0221527 A1 | 9/2008 | Bradley et al. |
| 2008/0221578 A1 | 9/2008 | Zeitani |
| 2008/0255613 A1 | 10/2008 | Kaiser et al. |
| 2008/0262544 A1 | 10/2008 | Burkhart |
| 2008/0268064 A1 | 10/2008 | Woodell-May |
| 2008/0269674 A1 | 10/2008 | Stone |
| 2008/0275477 A1 | 11/2008 | Sterrett et al. |
| 2008/0312689 A1 | 12/2008 | Denham et al. |
| 2009/0018589 A1 | 1/2009 | Smisson, III et al. |
| 2009/0018655 A1 | 1/2009 | Brunelle et al. |
| 2009/0054928 A1 | 2/2009 | Denham et al. |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0099598 A1 | 4/2009 | McDevitt et al. |
| 2009/0105754 A1 | 4/2009 | Sethi |
| 2009/0118774 A1 | 5/2009 | Miller, III |
| 2009/0118775 A1 | 5/2009 | Burke |
| 2009/0125073 A1 | 5/2009 | Rehm |
| 2009/0138002 A1 | 5/2009 | Fenton |
| 2009/0138054 A1 | 5/2009 | Teague et al. |
| 2009/0156997 A1 | 6/2009 | Trenhaile |
| 2009/0163949 A1 | 6/2009 | Rolnick et al. |
| 2009/0177233 A1 | 7/2009 | Malek |
| 2009/0192468 A1 | 7/2009 | Stone |
| 2009/0198277 A1 | 8/2009 | Gordon et al. |
| 2009/0204146 A1 | 8/2009 | Kaiser et al. |
| 2009/0228042 A1 | 9/2009 | Koogle, Jr. et al. |
| 2009/0234357 A1 | 9/2009 | Morales et al. |
| 2009/0234358 A1 | 9/2009 | Morales et al. |
| 2009/0240251 A1 | 9/2009 | Gabele |
| 2009/0240335 A1 | 9/2009 | Arcenio et al. |
| 2009/0248091 A1 | 10/2009 | Teague et al. |
| 2009/0265014 A1 | 10/2009 | May et al. |
| 2009/0306711 A1 | 12/2009 | Stone et al. |
| 2009/0312776 A1 | 12/2009 | Kaiser et al. |
| 2009/0318960 A1 | 12/2009 | Burkhart |
| 2009/0318961 A1 | 12/2009 | Stone et al. |
| 2010/0042114 A1 | 2/2010 | Schaffhausen |
| 2010/0087857 A1 | 4/2010 | Stone et al. |
| 2010/0145384 A1 | 6/2010 | Stone et al. |
| 2010/0191342 A1* | 7/2010 | Byrd et al. .................. 623/20.28 |
| 2010/0211075 A1 | 8/2010 | Stone |
| 2010/0256677 A1 | 10/2010 | Albertorio et al. |
| 2010/0268273 A1 | 10/2010 | Albertorio et al. |
| 2010/0268275 A1 | 10/2010 | Stone et al. |
| 2010/0270306 A1 | 10/2010 | Shiffer |
| 2010/0292792 A1 | 11/2010 | Stone et al. |
| 2010/0305698 A1 | 12/2010 | Metzger et al. |
| 2010/0312341 A1 | 12/2010 | Kaiser et al. |
| 2011/0009885 A1 | 1/2011 | Graf et al. |
| 2011/0087284 A1 | 4/2011 | Stone et al. |
| 2011/0098727 A1 | 4/2011 | Kaiser et al. |
| 2011/0106153 A1 | 5/2011 | Stone et al. |
| 2011/0160767 A1 | 6/2011 | Stone et al. |
| 2011/0160768 A1 | 6/2011 | Stone et al. |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0218625 A1 | 9/2011 | Berelsman et al. |
| 2011/0224799 A1 | 9/2011 | Stone |
| 2011/0264141 A1 | 10/2011 | Denham et al. |
| 2011/0270278 A1 | 11/2011 | Overes et al. |
| 2011/0270306 A1 | 11/2011 | Denham et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0059418 A1 | 3/2012 | Denham et al. |
| 2012/0095470 A1 | 4/2012 | Kaiser et al. |
| 2012/0123474 A1 | 5/2012 | Zajac et al. |
| 2012/0123541 A1 | 5/2012 | Albertorio et al. |
| 2012/0150297 A1 | 6/2012 | Denham et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0197271 A1 | 8/2012 | Astorino et al. |

FOREIGN PATENT DOCUMENTS

| | | |
|---|---|---|
| AU | 5850469 | 1/1971 |
| AU | 5963869 | 2/1971 |
| AU | 1505470 | 11/1971 |
| AU | 2223767 | 5/1973 |
| AU | 3615171 | 5/1973 |
| AU | 5028569 | 9/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| EP | 0108912 | 5/1984 |
| EP | 0129422 | 12/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |

| | | |
|---|---|---|
| EP | 0441065 | 8/1991 |
| EP | 0451932 | 10/1991 |
| EP | 0464480 | 1/1992 |
| EP | 0490417 A1 | 6/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0611551 A1 | 8/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 A | 9/1992 |
| GB | 2312376 | 10/1997 |
| GB | 2403416 A | 1/2005 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9503003 | 2/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03005914 A1 | 1/2003 |
| WO | WO-03071962 | 9/2003 |
| WO | WO-03077772 | 9/2003 |
| WO | WO-2004091412 A1 | 10/2004 |
| WO | WO-2005104992 A1 | 11/2005 |
| WO | WO-2008002550 A2 | 1/2008 |
| WO | WO-2009012021 A1 | 1/2009 |
| WO | WO-2011112371 A1 | 9/2011 |
| WO | WO-2011150238 A1 | 12/2011 |

OTHER PUBLICATIONS

"Do your next distal tendon repair with . . . The Lubbers Technique", Teno Fix® brochure, 2003 (2 pages) Ortheon® Medical.
"EZ Loc Femoral Fixation Device," copyright 2005 Arthrotek, Inc. (8 sheets).
"Make your next tendon repair an open-and-shut case. The Teno Fix® Tendon Repair System", Teno Fix® brochure, 2003 (2 pages) Ortheon® Medical.
"PANALOK Anchor with PDS II and ETHIBOND Suture", Mitek Products ETHICON, 1997.
"SE Graft Tensioning System Surgical Technique," Linvatec Corporation copyright 2003, 2004.
"Technique for ACL Reconstruction with Acufex Director Drill Guide and Endobutton CL," by Thomas D. Roseberg, copyright 1999 Smith & Nephew.
A. Weiler, et al; Biodegradierbare Interferenzschrauben in der Kreuzbandchirurgie; OP-JOURNAL 14 pp. 278-284; 1998.
Arthrotek, A Biomet Company; Knees; Sure fire Hybrid Meniscal Device.
Arthrotek, A Biomet Company; Sure fire Hybrid Meniscal Device; Launch Date: Fall AANA 2004.
Bio-Intrafix (TCP/PLA & Intrafix, Tibial Soft Tissue Fasteners, by DePuy Mitek, 6 sheets, (date unknown).
F. Alan Barber, M.D., "Uses and Abuses of Sutures and Anchors," Shoulder Scope, San Diego Shoulder Arthroscopy Library.
F. Alan Barber, M.D., "Using Sutures and Anchors," San Diego Shoulder Arthroscopy Course, 17th Annual Meeting.
Flavia Namie Azato, et al. "Traction endurance biomechanical study of metallic suture anchors at different insertion angles," Acta ortop. bras., vol. 11, No. 1, Sao Paulo, Jan./Mar. 2003.
Hecker AT, et al., "Pull-out strength of suture anchors for rotator cuff and Bankart lesion repairs," Am J Sports Med. 1993.
Invitation to Pay Additional Fees mailed Jun. 9, 2011 for PCT/US2011/026349 claiming benefit of U.S. Appl. No. 12/938,902, filed Nov. 3, 2010; and U.S. Appl. No. 12/719,337, filed Mar. 8, 2010.
Lawhorn, M.D., Keith, MaxFire™ Meniscal Repair Device with Zip Loop™ Technology, Biomet Sports Medicine, Feb. 29, 2008.
Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.
Opus Medical; The AutoCuff System; www.opusmedical.com; 2003.
Patrick Hunt, et al.; Development of a Perforated Biodegradable Interference Screw; Arthroscopy: The Journal of Arthroscopic and Related Surgery, vol. 21, No. 3; pp. 258-265; Mar. 2005.
Roy Alan Majors, M.D.; "Meniscal repairs: proven techniques and current trends," Lippincott Williams & Wilkins, Inc.; 2002.
Shoulder Arthroscopy; pp. H-2-H-22.
Smith & Nephew Endoscopy, "Endoscopic Meniscal Repair Using the T-Fix;" 1996.
Smith & Nephew, "Fast-Fix," Meniscal Repair System; 2001.
Stuart E. Fromm, M.D., RapidLoc, Meniscal Repair System, Mitek Products, Ethicon, 2001.
ToggleLoc™, Femoral Fixation Device, Arthrotek, Mar. 31, 2006.
"AperFix® System Surgical Technique Guide. Single Tunnel Double Bundle. ™" Cayenne Medical brochure. (Aug. 2008) 8 sheets.
"Bio-Intrafix Tibial Soft Tissue Fasteners, Building on the Legacy of IntraFix," brochure. DePuy Mitek,(Feb. 2007) 6 sheets.

"Biomechanical Evaluation of the Biomet Sports Medicine JurggerKnot™ Soft Anchor in Porcine Bone," Study completed Jan. 2010. Biomet Sports Medicine Research and Development, Warsaw, Indiana. 2 pages.

"JuggerKnot™ Soft Anchor Midfoot Repair," brochure. Biomet Sports Medicine (Jul. 2011) 12 sheets.

"JuggerKnot™ Soft Anchor. It's Small. It's strong. And it's all suture . . . " Ordering Information brochure. Biomet Sports Medicine (Jun. 2011) 2 sheets.

"JuggerKnot™ Soft Anchor. Labral Repair," brochure. Biomet Sports Medicine (Apr. 2011) 12 sheets.

International Search Report and Written Opinion mailed Jul. 28, 2011 for PCT/US2011/026349 claiming benefit of U.S. Appl. No. 12/938,902, filed Nov. 3, 2010; and U.S. Appl. No. 12/719,337, filed Mar. 8, 2010.

International Search Report and Written Opinion mailed Oct. 14, 2011 for PCT/US2011/038188 filed May 26, 2011 claiming benefit of U.S. Appl. No. 12/788,973, filed May 27, 2010 and U.S. Appl. No. 12/788,966, filed May 27, 2010.

Invitation to Pay Additional Fees mailed Aug. 5, 2011 for PCT/US2011/038168 claiming benefit of U.S. Appl. No. 12/788,973, filed May 27, 2010 and U.S. Appl. No. 12/788,966, filed May 27, 2010.

"Arthroscopic Meniscal Repair using the Meniscal Cinch™", Surgical Technique brochure. (2008) Arthrex® 6 sheets.

Pioneer® Sternal Cable System (2010).

Rapid Sternal Closure (2006) KLS Martin L.P. http://www.rapidsternalclosure.com/medical/demo.php Web accessed Sep. 8, 2008.

Saxena, Pankaj, MCh, DNB et al., "Use of Double Wires in Sternal Closure, A Useful Technique," Texas Heart® Institute. Journal List> Tex Heart Inst J > v.33(4); (2006).

Zeitani, Jacob, M.D., "A New Sternal Reinforcement Device to Prevent and Treat Sternal Dehiscence," CTSNet.org (Jun. 30, 2008).

Invitation to Pay Additional Fees mailed Jul. 19, 2012, for PCT/US2012/037703 claiming benefit of U.S. Appl. No. 13/109,667, filed May 7, 2011.

* cited by examiner

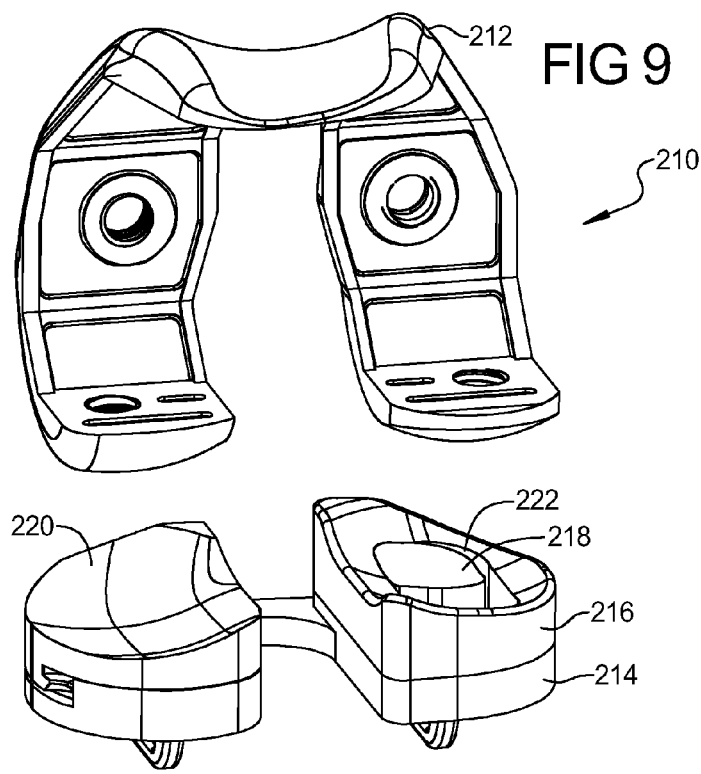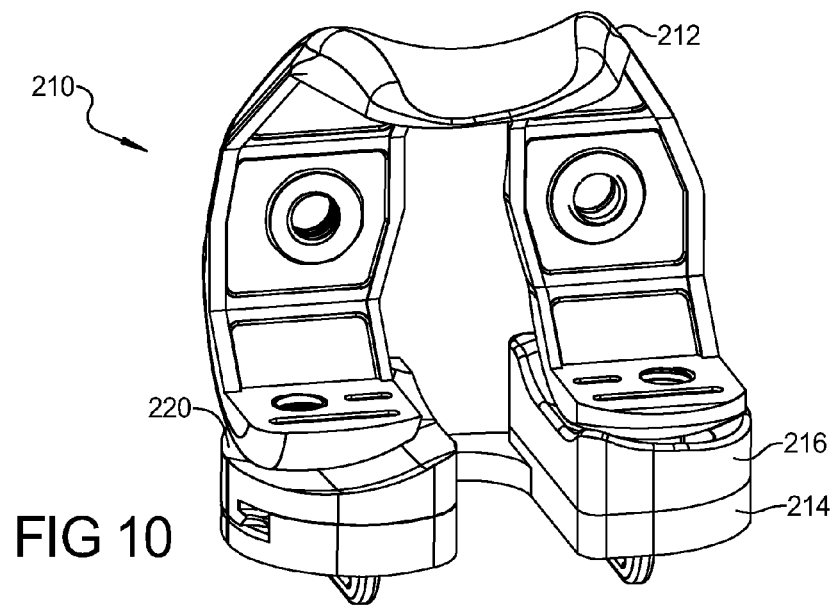

FIG 11
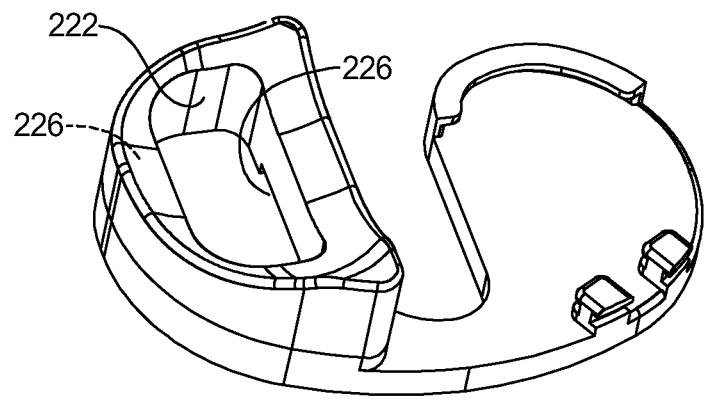
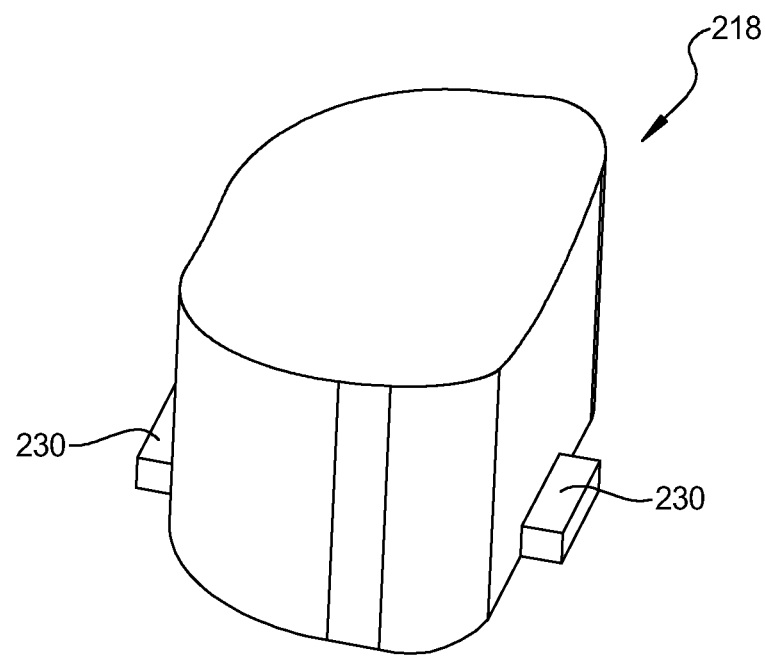
FIG 12

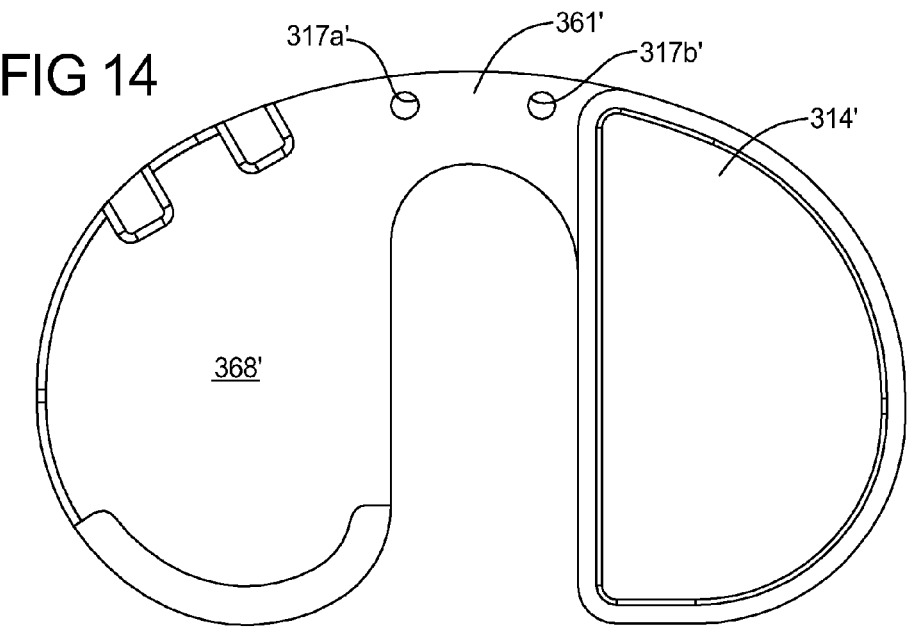
FIG 14
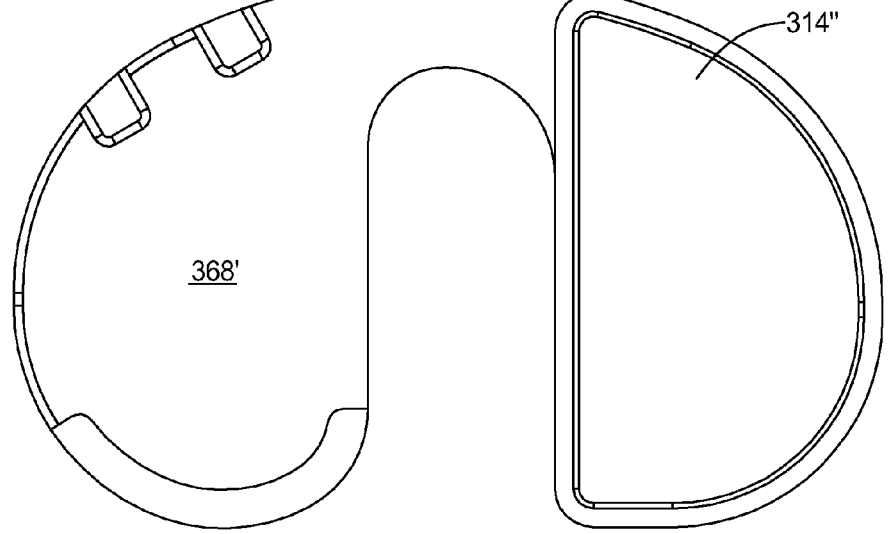
FIG 15

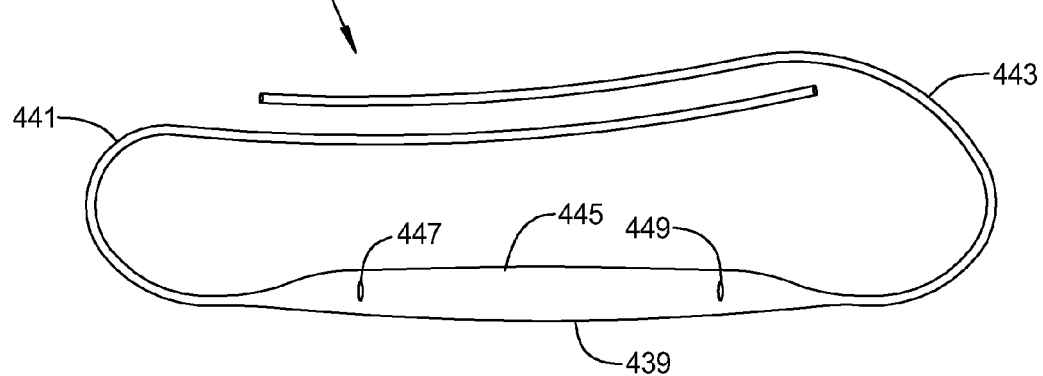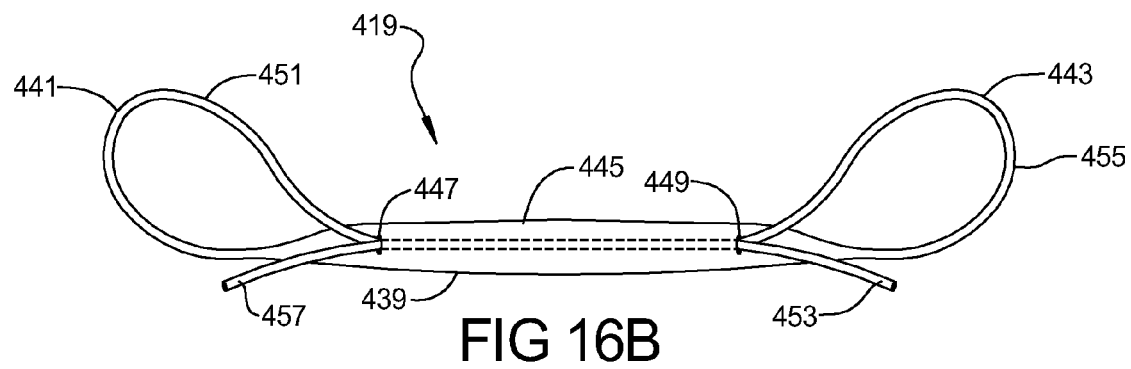

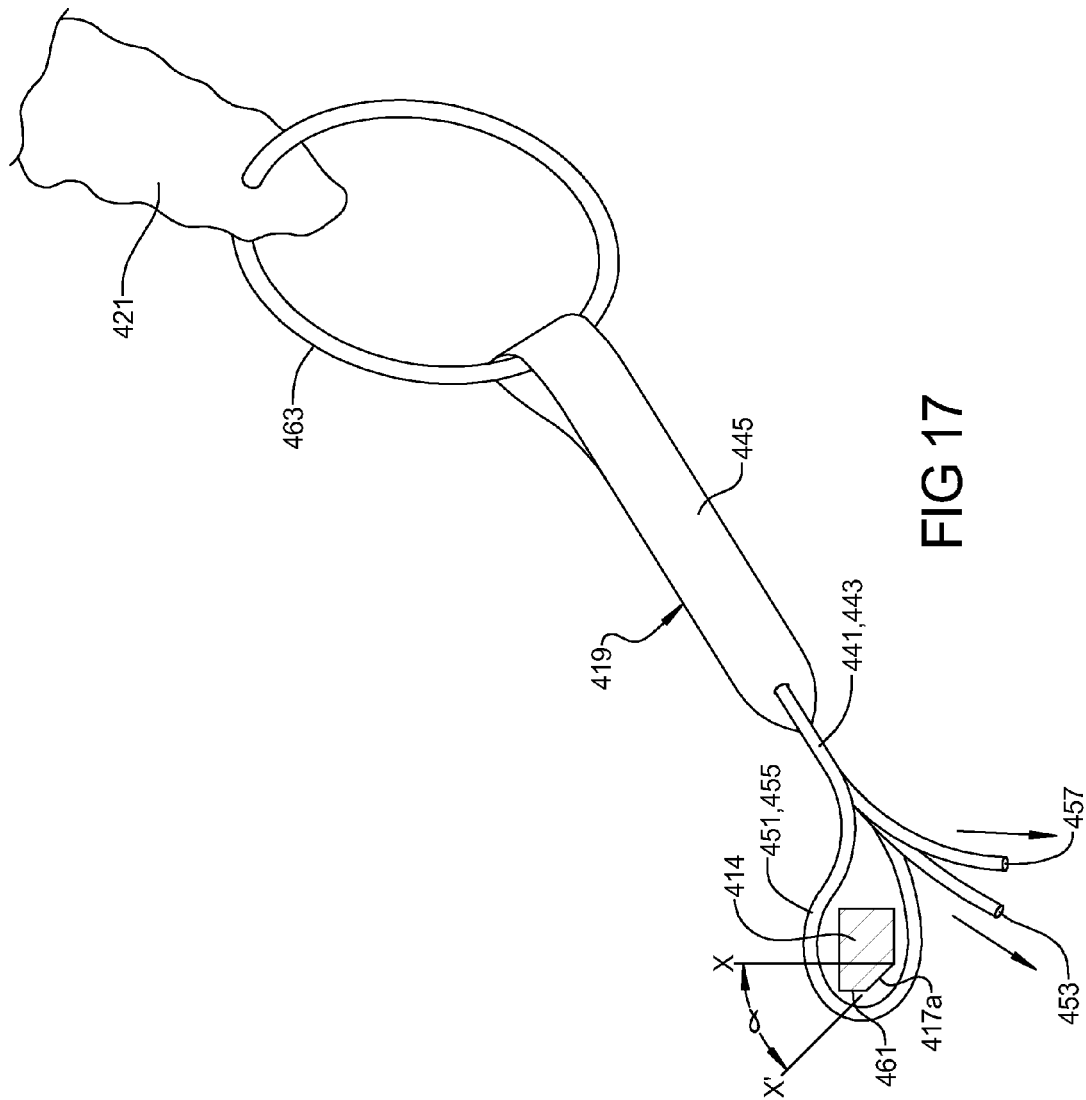

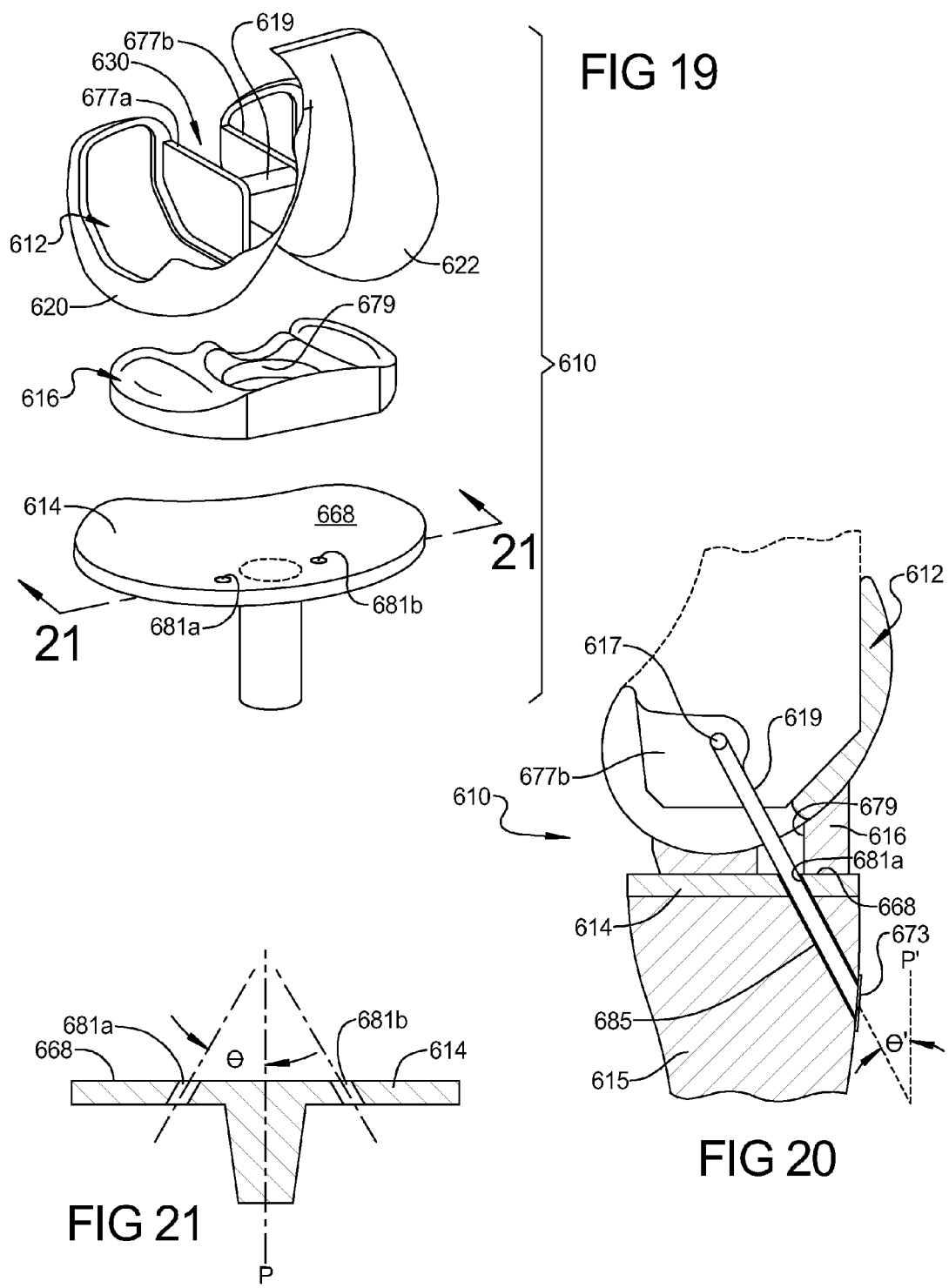

KNEE PROSTHESIS ASSEMBLY WITH LIGAMENT LINK

CROSS REFERENCE TO RELATED APPLICATION

This application claims the benefit of U.S. Provisional Application No. 61/181,938, filed on May 28, 2009, the entire disclosure of which is incorporated herein by reference.

This application is a continuation-in-part of U.S. patent application Ser. No. 12/489,168 filed on Jun. 22, 2009, which is a continuation-in-part of U.S. patent application Ser. No. 12/474,802 filed on May 29, 2009, which is a continuation-in-part of (a) U.S. patent application Ser. No. 12/196,405 filed on Aug. 22, 2008; (b) U.S. patent application Ser. No. 12/196,407 filed on Aug. 22, 2008; (c) U.S. patent application Ser. No. 12/196,410 filed on Aug. 22, 2008; and (d) a continuation-in-part of U.S. patent application Ser. No. 11/541,506 filed on Sep. 29, 2006, which is now U.S. Pat. No. 7,601,165 issued on Oct. 13, 2009.

This application is a continuation-in-part of U.S. patent application Ser. No. 12/570,854 filed on Sep. 30, 2009, which is a continuation-in-part of (a) U.S. patent application Ser. No. 12/014,399 filed on Jan. 15, 2008; and (b) U.S. patent application Ser. No. 12/014,340 filed on Jan. 15, 2008.

This application is a continuation-in-part of U.S. patent application Ser. No. 12/702,067 filed on Feb. 8, 2010, which is a continuation of U.S. patent application Ser. No. 11/541,505 filed on Sep. 29, 2006 and is now U.S. Pat. No. 7,658,751 issued on Feb. 9, 2010.

This application is a continuation-in-part of U.S. patent application Ser. No. 12/196,398 filed Aug. 22, 2008, which is a continuation-in-part of U.S. patent application Ser. No. 11/784,821 filed Apr. 10, 2007.

The disclosures of all the above applications are incorporated by reference herein.

FIELD

The following relates to a knee prosthesis assembly and, more particularly, to a knee prosthesis assembly with a ligament link.

BACKGROUND

The statements in this section merely provide background information related to the present disclosure and may not constitute prior art.

Prosthetic joints can reduce pain due to arthritis, anatomical deterioration, deformation, and the like. By replacing or strengthening the anatomy, prosthetic joints can improve mobility of the joint.

Anatomical knee joints may leave intact a plurality of anatomical ligaments, which extend between and connect the bones of the knee joint. In some cases, the prosthetic knee joint can be implanted, leaving one or more of these anatomical ligaments intact. In other cases, if an anatomical ligament is compromised, the ligament is removed and a more constrained prosthetic knee joint is implanted.

In other instances where there is only soft tissue damage, an end of an anatomical ligament that has become disconnected from bone can be reattached to the bone with a fastener. Also, in some cases, the anatomical ligament can be resected and at least a portion of the resected ligament can be replaced by an autograft, allograft, xenograft, or artificial graft. These grafts can be attached to a remaining portion of the anatomical ligament and/or to bone using a fastener, etc.

The following disclosure relates to a knee prosthesis assembly that restores function of a resected and/or removed anatomical ligament. The knee prosthesis assembly of the present disclosure can be quickly and conveniently implanted.

SUMMARY

A prosthetic knee joint assembly for a knee joint with a tibia and a femur is disclosed. The assembly includes a femoral component that engages the femur and at least one bearing that supports articulation of the femoral component thereon. Also, the assembly includes a tibial tray that supports the bearing and engages the tibia. The assembly also includes a ligament link coupling component included on the femoral component or the tibial tray. The assembly additionally includes a ligament link operably coupled to the one of the tibial tray or the femoral component via the ligament link coupling component. The ligament link also extending through the other of the femoral component or the tibial tray to operably couple to the respective one of the femur or the tibia. The ligament link extends from a first end to a second end, and the ligament link has an outer wall defining an interior longitudinal passage portion. The ligament link also has a first aperture passing through the outer wall and disposed between the first and second ends, the ligament link additionally has a second aperture passing through the outer wall and disposed between the first and second ends. The first end extends through the first and second apertures and the longitudinal passage portion to define a first adjustable loop, and the second end extends through the first and second apertures and the longitudinal passage portion to define a second adjustable loop.

A method of implanting a prosthetic knee joint assembly is also disclosed. The method includes operably coupling a femoral component of the knee joint assembly to a femur of a patient. The method also includes operably coupling a tibial component of the knee joint assembly to a tibia of the patient. Furthermore, the method includes operably coupling a ligament link to one of the femur or the tibia. In addition, the method includes operably coupling the ligament link directly to one of the tibial component or the femoral component via a ligament link coupling component included on the one of the tibial component or the femoral component. The ligament link extends from a first end to a second end, and the ligament link has an outer wall defining an interior longitudinal passage portion. The ligament link also has a first aperture passing through the outer wall and disposed between the first and second ends, the ligament link additionally has a second aperture passing through the outer wall and disposed between the first and second ends. The first end extends through the first and second apertures and the longitudinal passage portion to define a first adjustable loop, and the second end extends through the first and second apertures and the longitudinal passage portion to define a second adjustable loop.

Still further, a prosthetic knee joint assembly for a knee joint of a patient with a tibia and a femur is disclosed. The prosthetic knee joint assembly includes a femoral component that engages the femur. The femoral component includes a medial and lateral condyle portion connected by a patellar track portion as well as an intercondylar opening defined between the medial and lateral condyle portions. Also, the assembly includes at least one bearing that supports articulation of at least one of the medial and lateral condyle portions thereon. Moreover, the assembly includes a tibial tray that supports the bearing and that engages the tibia. The tibial tray includes a plurality of coupling components, and the coupling components are disposed on an anterior portion of the tibial tray. The coupling components are disposed on opposite sides of a medial plane of the tibial tray. Additionally, the assembly includes a ligament link operably coupled to the tibial tray via the coupling component. The ligament link is also operable to couple to the femur. The ligament link extends through the intercondylar opening, and the ligament link extends from a first end to a second end. The ligament link has an outer wall defining an interior longitudinal passage portion, and the ligament link also includes a first aperture passing through the outer wall and disposed between the first and second ends. The ligament link also includes a second aperture passing through the outer wall and disposed between the first and second ends. The first end extends through the first and second apertures and the longitudinal passage portion to define a first adjustable loop and a first free end. The second end extends through the first and second apertures and the longitudinal passage portion to define a second adjustable loop and a second free end. The first and second free ends are pullable to increase a tension in the ligament link.

Moreover, a prosthetic knee joint assembly for a knee joint of a patient with a tibia and a femur is disclosed. The prosthetic knee joint assembly includes a femoral component that engages the femur. The femoral component includes a first condylar portion and a second condylar portion separated at a distance apart to define an intercondylar opening. The femoral component includes a ligament link coupling component extending from at least one of the first and second condylar portions into the intercondylar opening. Additionally, the assembly includes at least one bearing that supports articulation of the femoral component thereon and a tibial tray that engages the tibia. The tibial tray includes a superior surface that supports the bearing thereon, and the tibial tray includes an opening. Furthermore, the assembly includes a ligament link operably coupled to the femoral component via the coupling component. The ligament link also extends through the opening to operably couple to the tibia. Additionally, the ligament link extends from a first end to a second end and has an outer wall defining an interior longitudinal passage portion. The ligament link includes a first aperture passing through the outer wall and disposed between the first and second ends. The ligament link also includes a second aperture passing through the outer wall and disposed between the first and second ends. The first end extends through the first and second apertures and the longitudinal passage portion to define a first adjustable loop and a first free end. Also, the second end extends through the first and second apertures and the longitudinal passage portion to define a second adjustable loop and a second free end. The first and second free ends are pullable to increase a tension in the ligament link.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 9 is a partially exploded posterior view of a knee prosthesis constructed in accordance to additional features of the present teachings;

FIG. 10 is a posterior perspective view of the knee prosthesis of FIG. 9;

FIG. 11 is an anterior perspective view of a tibial tray and fixed bearing portion of the knee prosthesis of FIG. 10;

FIG. 12 is a perspective view of a mobile bearing that slidably cooperates within a pocket formed on the fixed bearing of FIG. 11;

FIG. 14 is a top view of a tibial tray of the knee prosthesis of FIG. 13 according to various other exemplary embodiments;

FIG. 15 is a top view of a tibial tray of the knee prosthesis of FIG. 13 according to various other exemplary embodiments;

FIGS. 16A and 16B are top views of a portion of a ligament link according to various embodiments for the knee prosthesis of the present teachings, wherein FIG. 16A shows the portion in an unlooped state and FIG. 16B shows the portion in a looped state;

FIG. 17 is a section view of the knee prosthesis of FIG. 13 according to various other exemplary embodiments;

FIG. 19 is an exploded, perspective view of another knee prosthesis assembly according to additional embodiments of the present disclosure;

FIG. 20 is a cross sectional view of the knee prosthesis assembly of FIG. 19; and FIG. 21 is a cross sectional view of the tibial component of the knee prosthesis assembly of FIG. 19 taken along the line 21-21.

DETAILED DESCRIPTION

Figure 1:
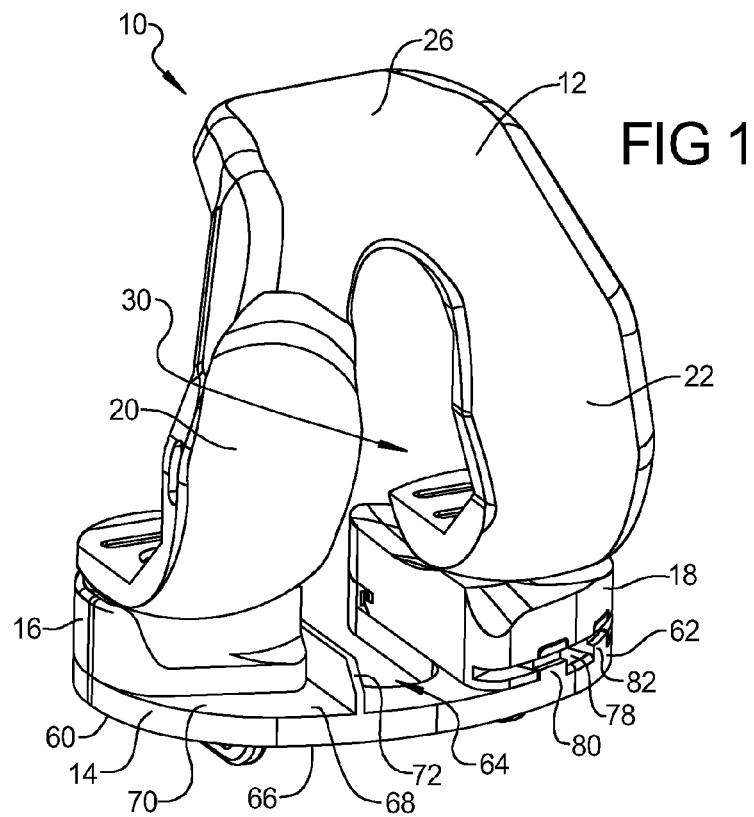
FIG. 1 is an anterior perspective view of a knee prosthesis assembly according to various exemplary embodiments of the present disclosure.

The following description is merely exemplary in nature and is not intended to limit the present disclosure, application, or uses. It should be understood that throughout the drawings, corresponding reference numerals indicate like or corresponding parts and features.

Figure 2:
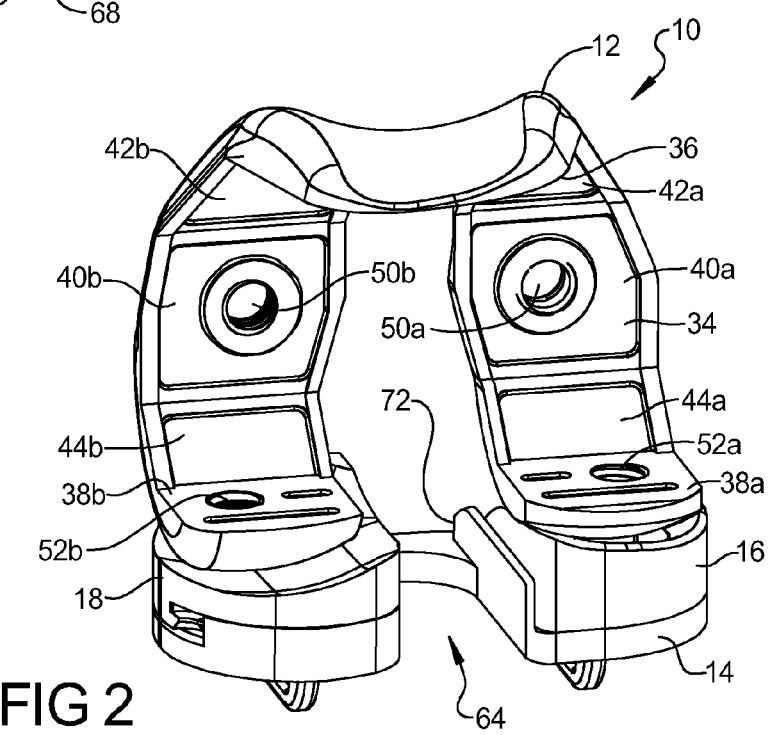
FIG. 2 is a posterior perspective view of the knee prosthesis of FIG. 1.

With initial reference to FIGS. 1 and 2, a knee prosthesis assembly constructed in accordance to one example of the present teachings is shown and generally identified at reference numeral 10. The knee prosthesis assembly 10 can generally include a femoral component 12, a tibial tray 14, a first bearing 16 (a medial bearing), and a second bearing 18 (a lateral bearing). As will be described, the knee prosthesis assembly 10 can be used when it is desirable to retain or reconstruct an anterior cruciate ligament (ACL) and/or a posterior cruciate ligament (PCL). Although the illustrated prosthesis assembly 10 is intended for a left knee of a patient, it will be appreciated that the prosthesis assembly 10 could include similar features to be configured for implantation in a right knee of a patient as well.

The respective components of the knee prosthesis assembly 10 can be patient specific, such that each component can be constructed for optimal features for a given patient. For example, the bone interface margins of the femoral component 12 and tibial tray 14 can be patient specific for optimized bone coverage. In addition, the overall size, such as anterior-posterior dimensions and bone cut geometry can be determined and used for manufacturing the components of the knee prosthesis assembly 10. Moreover, some articulation features can be determined and used as criteria for forming the components of the knee prosthesis assembly 10. In sum, each of the components of the knee prosthesis assembly 10 can be a patient-specific implant, a semi-custom implant or an off-the-shelf or standard production implant. A custom-made implant is a patient-specific, one-of-a-kind implant specifically made for a particular patient, and consequently there is no inventory associated with such implant. Standard or off-the-shelf implants are available and stocked in a number of sizes, typically six or more, and a number of configurations or types, including bilateral or unilateral implants, constrained, semi-constrained, mobile, etc. Because of the variety of sizes and configurations that are kept in stock for different patients, a large inventory of standard implants is created, and several molds for each type and size of implant may be used. Semi-custom implants can provide an intermediate solution between custom-made and off-the-shelf implants. Semi-custom implants reduce the size of inventory and molds required for production, while allowing some degree of patient-specific customization. Additional description of patient-specific implants and semi-custom implants and their implementations may be found in copending patent application Ser. No. 12/103,824, filed Apr. 16, 2008 and entitled: Method and Apparatus for Manufacturing An Implant, the disclosure of which is hereby incorporated by reference in its entirety.

Figure 3:
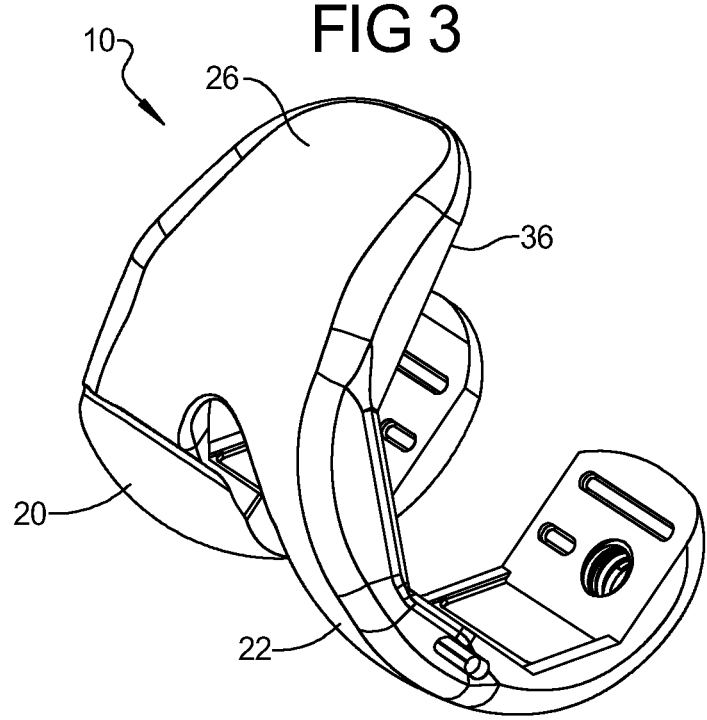
FIG. 3 is a lateral perspective view of a femoral component of the knee prosthesis of FIG. 1.

With additional reference to FIG. 3, the femoral component 12 will now be described in greater detail. The femoral component 12 can generally comprise a cruciate retaining prosthesis and can include various portions to replace or mimic the distal femur. The femoral component 12 can include a medial condyle portion 20 and a lateral condyle portion 22. The condyle portions 20, 22 can include a convex, rounded contact surface that extends generally in an anterior/posterior direction similar to anatomical condyles. The condyle portions 20, 22 can respectively replace the anatomical medial and lateral condyles of a distal femur. The condyle portions 20, 22 can be connected by a patellar track portion 26. Thus, the femoral component 12 can be generally U-shaped and curved in the superior direction. The condyle portions 20, 22 and patellar track portion 26 can be integrally connected so as to be monolithic. The patellar track portion 26 can allow for articulation of a patella (not shown), either natural or prosthetic, once the femoral component 12 is implanted onto the distal femur. The condyle portions 20, 22 and the patellar track portion 26 can generally define an exterior portion of the femoral component 12. The femoral component 12 can define an intercondylar opening 30 or passage between the medial and lateral condyle portions 20, 22 (i.e., the open and unobstructed area disposed posteriorly from the patellar track portion 26).

As will be discussed, the opening 30 can accommodate and provide clearance for an anatomical anterior cruciate ligament (ACL) and/or an anatomical posterior cruciate ligament (PCL). Furthermore, as will be discussed, the opening 30 can accommodate and provide clearance for a ligament link (e.g., an autograft, an allograft, a xenograft, an artificial graft, or a combination thereof) for reconstructing and restoring function of the anatomical ACL and/or PCL.

The femoral component 12 can include a bone contacting or superior surface 34 (FIG. 2). The superior surface 34 can include an anterior surface 36 that can be substantially flat and formed generally parallel to a pair of posterior surfaces 38a, 38b. A pair of intermediate surfaces 40a, 40b are provided generally at an intermediate portion of the superior surface 34. A pair of angled anterior transition surfaces 42a, 42b can generally connect the anterior surface 36 with the intermediate surfaces 40a, 40b. Similarly, a pair of angled posterior transition surfaces 44a, 44b can be provided between the respective posterior surfaces 38a, 38b and the intermediate surfaces 40a, 40b. In one example, a threaded boss 50a, 50b can be provided on each of the intermediate surfaces 40a, 40b, respectively. Similarly, a threaded boss 52a, 52b can be provided on the posterior surfaces 38a, 38b, respectively. The bosses 50a, 50b, 52a, 52b can be optionally used to threadably couple with various augments (not specifically shown) as necessary.

The femoral component 12 can be formed as a unitary structure and cast of a biocompatible high strength alloy, such as cobalt-chromium-molybdenum alloy or similar suitable material. All surfaces, which do not contact the femur, can be highly polished to provide smooth articulating bearing surfaces. The superior surface 34 of the femoral component 12 can be roughened or uneven or include porous material to allow bone ingrowth or attachment with bone cement. Other features of the femoral component 10 can include those associated with the Oxford® Partial Knee, which is marketed by Biomet, Inc. of Warsaw, Ind.

With reference now to FIGS. 1, 2, 4 and 5, the tibial tray 14 will now be described in greater detail. The tibial tray 14 can include a generally U-shaped body having a medial portion 60 and a lateral portion 62. An anterior portion 61 can extend between and can connect to both the medial and lateral portions 60, 62. The medial, anterior, and lateral portions 60, 61, 62 can be integrally connected so as to be monolithic. As will be discussed, the open and unobstructed area disposed posteriorly from the anterior portion 61 and between the medial and lateral portions 60, 62 can provide clearance for an anatomical anterior cruciate ligament (ACL), an anatomical posterior cruciate ligament (PCL), or a ligament link (e.g., an autograft, an allograft, a xenograft, an artificial graft, or a combination thereof) for reconstructing and restoring function of the anatomical ACL and/or PCL.

A slot 64 can be defined in the tibial tray 14 generally between the medial, anterior, and lateral portions 60, 61, 62. As with the intercondylar opening 30 of the femoral component 12, the slot 64 of the tibial tray 14 can accommodate and provide a clearance for an anatomical ACL, an anatomical PCL, and/or a ligament link (e.g., autograft, allograft, xenograft, artificial graft, or combination thereof). In other embodiments that will be discussed, a ligament link can be operably coupled directly to the tibial tray 14.

During implantation, the tibial tray 14 can be advanced posteriorly, such that the slot 64 can accommodate the anatomical ACL, anatomical PCL, and/or ligament link. In instances where a ligament link is used to reconstruct the anatomical ACL and/or anatomical PCL, a trial tibial tray (as well as trial bearings, etc.) having corresponding geometries can be utilized. One suitable configuration is further described in commonly owned in U.S. Pat. No. 7,255,715, issued Aug. 14, 2007, which is hereby incorporated by reference in its entirety.

Figure 4:
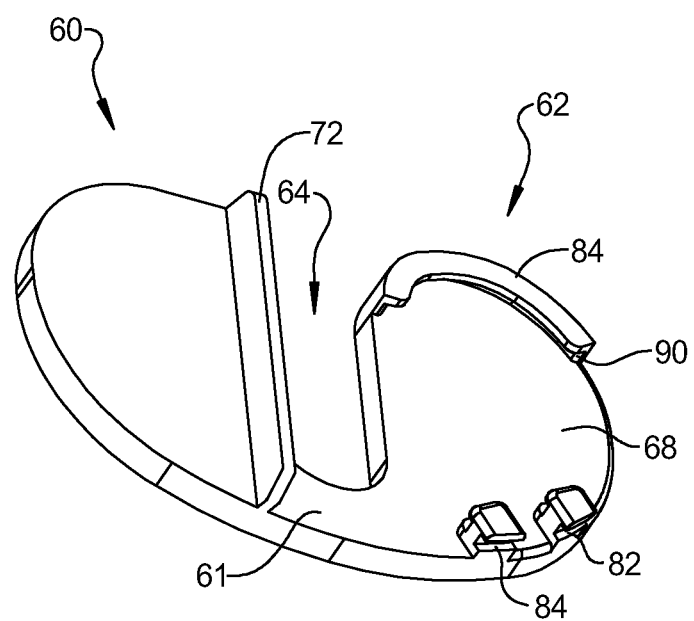
FIG. 4 is a superior perspective view of a tibial tray of the knee prosthesis of FIG. 1.
Figure 5:
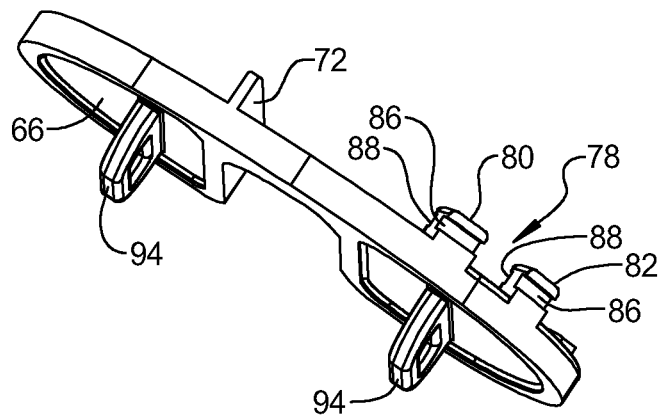
FIG. 5 is an inferior perspective view of the tibial tray of FIG. 4.

The tibial tray 14 can include an inferior bone engaging side 66 (FIG. 5) and a superior bearing engaging side 68 (FIG. 4). The medial portion 60 of the superior bearing engaging side 68 can include a highly polished tibial bearing surface 70. A rail 72 can extend in a generally anterior/posterior direction adjacent to the highly polished tibial bearing surface 70. The lateral portion 62 can include engaging structure 78 provided on the superior bearing engaging side 68. The engaging structure 78 can include a pair of posts 80, 82 integrally formed at an anterior edge thereof. A retaining rail 84 can extend superiorly from a posterior edge of the lateral portion 62. The posts 80, 82 can both have an anterior groove 86 and a posterior groove 88, respectively. The retaining rail 84 can have a transverse groove 90 formed on an inwardly facing surface. The tibial tray 14 can be generally manufactured of cobalt-chromium-molybdenum alloy or other suitable biocompatible material. A pair of fins 94 can extend from the inferior bone engaging side 66. While fins 94 are shown operatively associated with the tibial tray 14, other structures suitable for engaging a proximal tibia can include pegs, posts or porous material can additionally or alternatively be provided on the inferior bone engaging side 66.

The bearings 16, 18 will now be discussed in greater detail. In the embodiments shown in FIGS. 1 and 2, the first bearing 16 (medial floating bearing) is moveably supported by the tibial tray 14, and the second bearing 18 (lateral fixed bearing) is fixedly supported by the tibial tray 14. However, it will be appreciated that the first and second bearings 16, 18 could both be fixedly supported by the tibial tray 14 without departing from the scope of the present disclosure. Moreover, it will be appreciated that both bearings 16, 18 could be moveably supported by the tibial tray 14. Additionally, while the embodiment shown in the figures includes a floating bearing provided on a medial side and a fixed bearing provided on a lateral side, the location of these bearings can be swapped. Still further, it will be appreciated that the assembly 10 could include a single, monolithic bearing (floating or fixed) that extends across each of the medial, anterior, and lateral portions 60, 61, 62 of the tibial tray 14 while still providing clearance for the slot 64 without departing from the scope of the present disclosure.

Figure 6:
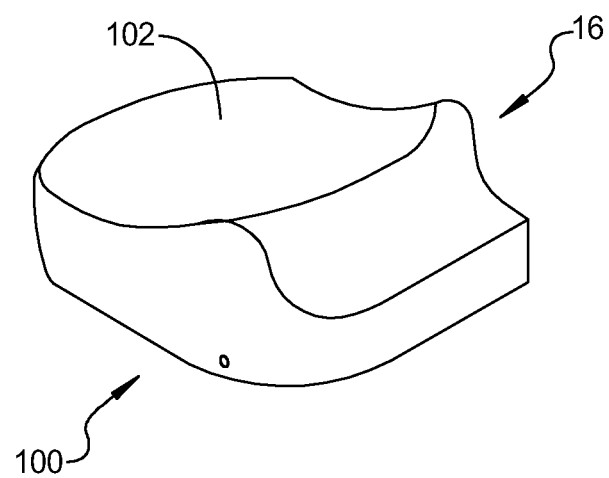
FIG. 6 is a perspective view of a mobile bearing of the knee prosthesis of FIG. 1.

With reference to FIGS. 1, 2 and 6, the embodiment of the first bearing 16 will now be described in greater detail. The first bearing 16 has a substantially planar inferior bearing surface 100 which slidably moves and articulates relative to the highly polished tibial bearing surface 70. The first bearing 16 further includes a first bearing surface 102. The first bearing surface 102 articulates with the medial condyle portion 20 of the femoral component 12. The first bearing 16 can be formed from a surgical grade, low friction, and low wearing plastic, such as ultra high molecular weight polyethylene (UHMWPE) or other suitable material.

Figure 7:
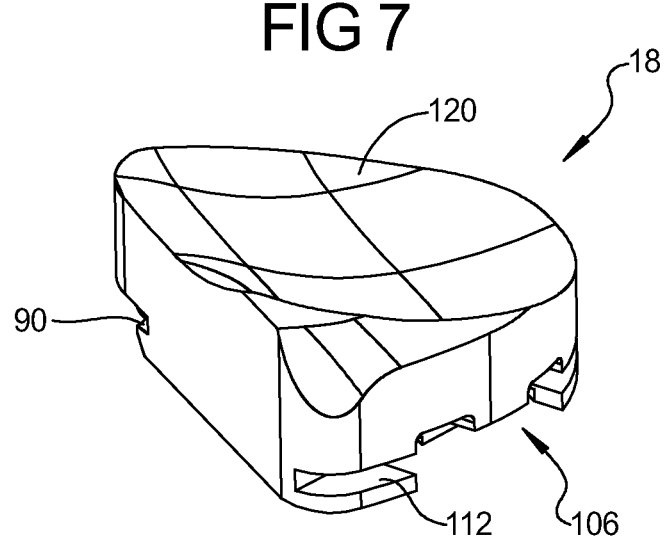
FIG. 7 is a perspective view of a fixed bearing of the knee prosthesis of FIG. 1.
Figure 8:
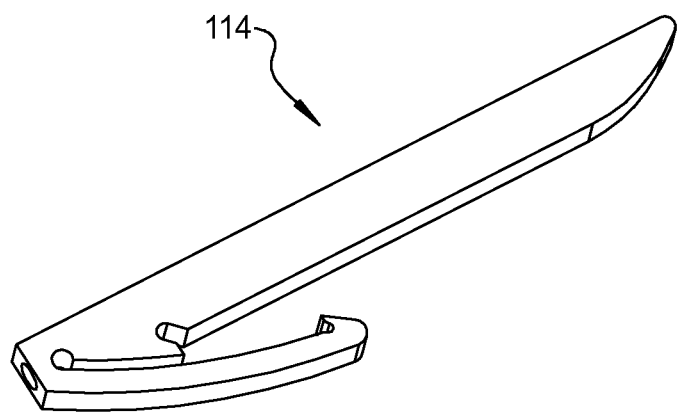
FIG. 8 is a perspective view of a locking bar associated with the fixed bearing of a knee prosthesis of FIG. 1.

With reference to FIGS. 1, 2 and 7, the second bearing 18 can include engaging structure 106 formed on an inferior surface for coupling with the engaging structure 78 provided on the lateral portion 62 of the tibial tray 14. The engaging structure 106 can generally include a posteriorly extending lip 110 and an anterior groove 112. A locking bar 114 (FIG. 8) can be slidably inserted through the slot 112 to interlock between the respective grooves 86 to capture the second bearing 18 to the lateral portion 62 of the tibial tray 14. The posteriorly extending lip 110 can be nestingly received by the retaining rail 84. The second bearing 18 can include a second bearing surface 120. The second bearing surface 120 can articulate with the lateral condyle portion 22 of the femoral component 12. The second bearing 18 can be formed from a surgical grade, low friction and low wearing plastic, such as UHMWPE or other suitable material.

During use, the medial and lateral condyle portions 20, 22 of the femoral component 12 can articulate on the first and second bearing surfaces 102, 120 of the respective bearings 16, 18. As can be appreciated, the second bearing 18 is static relative to the tibial tray 14 during articulation of the femoral component 12. The first bearing 16 is free to slide along the highly polished tibial bearing surface 70 of the medial portion 60 of the tibial tray 14. Movement of the first bearing 16 is limited by an inboard side of the rail 72.

Turning now to FIGS. 9-11, a knee prosthesis assembly constructed in accordance to additional features of the present teachings is shown and generally identified at reference numeral 210. The knee prosthesis assembly 210 can generally include a femoral component 212, a tibial tray 214, a medial side having a fixed bearing 216 that cooperates with a mobile bearing 218 and a lateral side having a fixed bearing 220. The femoral component 212 can be constructed similar to the femoral component 12 described above. The fixed bearing 220 can be constructed similar to the lateral fixed bearing 18 described above. The mobile bearing 218 can provide articulation that is fully conforming with the femoral component 212. The mobile bearing 218 can be captured around its perimeter by a pocket 222 formed by the fixed bearing 216. In this way, the mobile bearing 218 can have a reduced likelihood of becoming dislocated relative to the fixed bearing 216. While the fixed bearing 216 and mobile bearing 218 are shown generally associated with the lateral side of the tibial tray 214, such a configuration can be additionally or alternatively provided on the medial portion of the tibial tray 214. In one example, the mobile bearing 218 can be formed by polyethylene or polyetheretherketone (PEEK). As shown in FIG. 11, the fixed bearing 216 can have a pair of channels 226 formed thereon for guiding tabs 230 provided on the mobile bearing 218 (FIG. 12).

Figure 13:
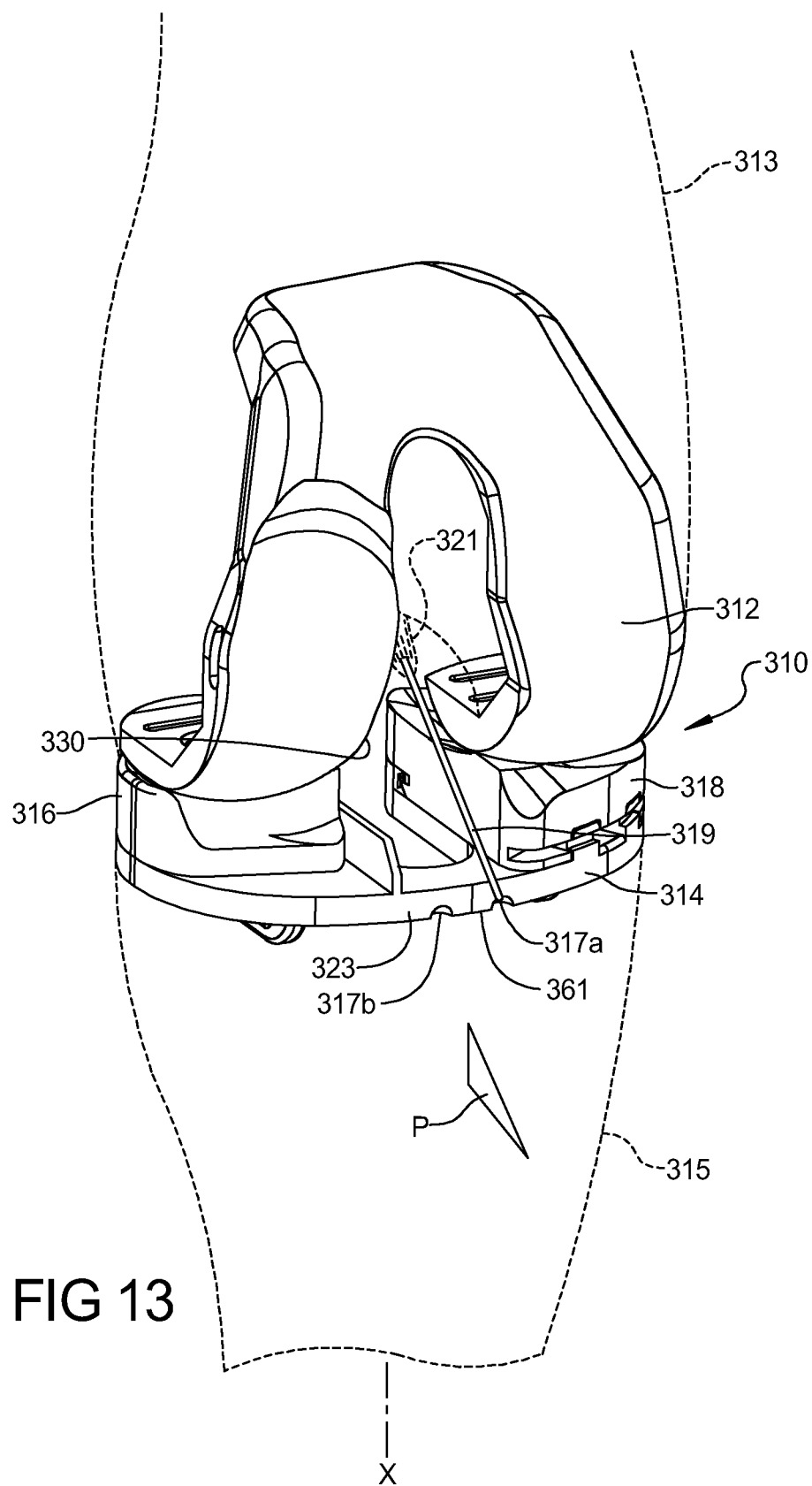
FIG. 13 is a perspective view of a knee prosthesis constructed in accordance to additional features of the present teachings.

Referring now to FIG. 13, a knee prosthesis assembly constructed in accordance to additional features of the present teachings is shown and generally identified at reference numeral 310. Components that correspond to the components of the embodiments of FIGS. 1-8 are indicated with corresponding reference numerals increased by 300. The assembly 310 can incorporate any of the features disclosed in Applicant's co-pending U.S. patent application Ser. No. 12/788, 966, filed May 27, 2010, which published as U.S. Patent Publication No. 2010/0305698 on Dec. 2, 2010, entitled KNEE PROSTHESIS ASSEMBLY WITH LIGAMENT LINK, and U.S. patent application Ser. No. 12/788,978, filed May 27, 2010, which published as U.S. Patent Publication No. 2010/0292792 on Nov. 18, 2010, entitled PROSTHETIC LIGAMENT SYSTEM FOR KNEE JOINT, both of which are filed concurrently herewith, and each of which is incorporated by reference in its entirety.

The knee prosthesis assembly 310 is shown relative to a resected anatomical femur 313 and a resected anatomical tibia 315, each of which are shown in phantom. The knee prosthesis assembly 310 can operatively and moveably couple to the resected anatomical femur 313 and the resected anatomical tibia 315 in order to support movement of the knee joint.

Also, the prosthesis assembly 310 is shown relative to an anatomical resected ligament 321, which is shown in phantom. In the embodiments represented in FIG. 13, the ligament 321 can be an anterior cruciate ligament (ACL), which is attached to the femur 313 and which has been resected or otherwise detached from the tibia 315. However, it will be appreciated that the ligament 321 could be of any suitable type, such as a posterior cruciate ligament (PCL), without departing from the scope of the present disclosure. It will also be appreciated that the ligament 321 could be intraoperatively resected from the tibia 315 while the prosthesis assembly 310 is being implanted, or the ligament 321 could be detached from the tibia 315 before surgery, due to injury, etc.

As shown in FIG. 13, the prosthesis assembly 310 can also include a ligament link 319. The ligament link 319 can be an autograft, an allograft, a xenograft, an artificial graft, or any combination thereof. The ligament link 319 can be flexible, and can withstand relatively high tension. Also, the ligament link 319 can pierce and extend through the ligament 321. In other embodiments, the ligament link 319 can operably couple to the ligament 321 via fasteners (e.g., sutures, and the like). In still other embodiments, the ligament link 319 can be operably coupled directly to the femur 313 with the ligament 321 eliminated altogether. Furthermore, the ligament link 319 can operably couple to the tibial tray 314 in a manner to be discussed.

The femoral component 312 of the prosthesis assembly 310 can be substantially similar to the embodiments of FIGS. 1-11. As shown, the intercondylar opening 330 can provide clearance for the ligament 321 and the ligament link 319.

The bearings 316, 318 can also be substantially similar to the embodiments of FIGS. 1-11. Furthermore, the tibial tray 314 can be substantially similar to the embodiments of FIGS. 1-11, except the tibial tray 314 can include at least one or more coupling components 317a, 317b. As will be discussed, the coupling components 317a, 317b can operably couple to the ligament link 319.

The coupling components 317a, 317b can have any suitable shape, size, and location on the tibial tray 314. For instance, as shown in FIG. 13, the coupling components 317a, 317b can each be grooves or recesses that are disposed on the anterior portion 361 of the tibial tray 314. In addition, the coupling components 317a, 317b can be defined in an inferior, anterior edge 323 of the tray 314. Also, as shown in FIG. 17, the coupling components 317a, 317b can each have an axis X' that is disposed at a positive acute angle, α, relative to a longitudinal axis X of the tibia 315. Accordingly, the coupling component 317a, 317b can be oriented substantially normal to the force of tension in the ligament link 319 as will be discussed in greater detail below.

As shown in FIG. 13, a selected one of the coupling components 317a, 317b can receive the ligament link 319 and retain the ligament link 319 against movement in the medial-lateral direction. For instance, the ligament link 319 can loop or wrap around and be received in the selected coupling component 317a, 317b. Accordingly, the ligament link 319 can maintain necessary tension and can support movement of the knee joint.

It will be appreciated that the tibial tray 314 can include any number of coupling components 317a, 317b. As shown in the embodiments illustrated in FIG. 13, there can be two coupling components 317a, 317b that are spaced apart from each other on opposite sides of a median plane P of the tibial tray 314. It will be appreciated that the tibial tray 314 can be a universal tibial tray 314 that is suitable for implantation in either a patient's right knee or a patient's left knee. If the tibial tray 314 is implanted in a left knee, the coupling component 317a can be used to retain the ligament link 319, and if the tibial tray 314 is implanted in a right knee, the coupling component 317b can be used to retain the ligament link 319.

In additional embodiments represented in FIG. 14, the coupling components 317a', 317b' can each be through holes. As shown, the coupling components 317a', 317b' can have a linear axis and can extend axially through both the superior side 368' of the anterior portion 361' of the tibial tray 314' as well as the inferior side (not specifically shown in FIG. 14). Thus, the ligament link (not specifically shown in FIG. 14) can extend through either of the coupling components 317a', 317b' in order to operably couple to the tibial tray 314'. For instance, the ligament link can extend through the selected coupling component 317a', 317b' and can be knotted or tied to secure the ligament link.

In still other embodiments represented in FIG. 15, the coupling components 317a", 317b" can each be eyelets that selectively open and close. It will be appreciated that the coupling component 317b" is shown closed, and the coupling component 317a" is shown open in the embodiments of FIG. 15. More specifically, the coupling components 317a", 317b" can each include a respective clasp 331a", 331b". Each clasp 331a", 331b" can be hingeably attached at one end to the anterior portion 361" of the tibial tray 314". The opposite end of each clasp 331a", 331b" can be selectively secured to and detached from the anterior portion 361" of the tibial tray 314". When the clasp 331a", 331b" is closed, the respective coupling component 317a", 317b" can secure the ligament link (not specifically shown) to the tibial tray 314". On the other hand, when the clasp 331a", 331b" is open, the ligament link can move into the respective coupling component 317a", 317b".

It will be appreciated that the ligament link 319 can be attached to the tibial tray 314 by the manufacturer or by other personnel before implantation surgery. Thus, the assembly 310 can be implanted more efficiently because the surgeon or other medical professional need not spend time intraoperatively tying knots or otherwise attaching the ligament link 319 to the tibial tray 314.

In other embodiments, the surgeon can intraoperatively attach the ligament link 319 to the tibial tray 314. For instance, the surgeon can select a ligament link 319 for implantation from a plurality of different ligament links 319 based on a desired tension, geometry, material, or other characteristic of the ligament link 319. Then, the surgeon can intraoperatively attach the ligament link 319 to both the anatomical ligament 321 and the tibial tray 314.

Furthermore, the ligament link 319 can be an optional feature. For instance, if the surgeon chooses not to use the ligament link 319 (and assuming that the ligament link 319 is attached to the tibial tray 314 by the manufacturer), the surgeon can cut or simply remove the ligament link 319 from the tibial tray 314 before attaching the tibial tray 314 to the resected tibia 315. Accordingly, the tibial tray 314 can be very versatile.

Referring now to FIGS. 16A and 16B, additional features of the ligament link 419 according to the present teachings will be discussed. Components that correspond with those of the embodiments of FIG. 13 are identified with corresponding reference numerals increased by 100. It will be appreciated that the embodiment of the ligament link 419 shown in FIGS. 16A, 16B can be only a portion of the ligament link of the present disclosure.

As shown in FIG. 16A, the ligament link 419 can be elongate and flexible and can extend from a first end 441 to a second end 443. Furthermore, the ligament link 419 can have an outer wall 439 that defines a longitudinal passage portion 445, which is disposed between the first and second ends 441, 443. The longitudinal passage portion 445 can be hollow. Moreover, the ligament link 419 can include a first aperture 447 that extends through the wall 439 and that is disposed between the first and second ends 441, 443. Moreover, the ligament link 419 can include a second aperture 449 that extends through the wall 439 and that is disposed between the first and second ends 441, 443. More specifically, the first aperture 447 can be disposed between the first end 441 and the longitudinal passage portion 445, and the second aperture 449 can be disposed between the second end 443 and the longitudinal passage portion 445.

As shown in FIG. 16B, the first end 441 can extend through the first aperture 447, through the longitudinal passage portion 445, and out of the longitudinal passage portion 445 via the second aperture 449. Likewise, the second end 443 can extend through the second aperture 449, through the longitudinal passage portion 445, and out of the longitudinal passage portion 445 via the first aperture 447. As such, the first end 441 can define a first adjustable loop 451 and a first free end 453. Likewise, the second end 443 can define a second adjustable loop 455 and a second free end 457.

The ligament link 419 can be made out of any suitable material, such as a flexible, high-strength, braided material. In some embodiments, some of the fibers in the link 419 can be inelastic while other fibers in the link 419 can be elastic and resilient. Moreover, in some embodiments, the fibers within the link 419 can have varying diameters. In addition, the ligament link 419 can have any of the various features disclosed in U.S. Patent Application Publication No. 2009/0318961, published Dec. 24, 2009, the disclosure of which is hereby incorporated by reference in its entirety. Additionally, in some embodiments, the fibers within the link 419 can have material properties of the type disclosed in U.S. patent application Ser. No. 12/788,978, filed May 27, 2010, which published as U.S. Patent Publication No. 2010/0292792 on Nov. 18, 2010, which is entitled PROSTHETIC LIGAMENT SYSTEM FOR KNEE JOINT, which is filed concurrently herewith, and which is hereby incorporated by reference in its entirety.

As shown in FIG. 17, the ligament link 419 can operably couple to both the anatomical resected ligament 421 and the tibial tray 414. For instance, the ligament link 419 also includes a suture 463 or other fastener that is attached to the ligament 421. More specifically, the suture 463 can pierce the ligament 421, and the longitudinal passage portion 445 can extend through the suture 463 and can be folded such that both of the adjustable loops 451, 455 extend toward the tibial tray 414. The first and second adjustable loops 451, 455 can loop around the anterior portion 461 of the tibial tray 414 and can be retained within the coupling component 417a of the tibial tray 414. In other embodiments, the ligament link 419 can be coupled directly to the ligament 421 without the suture 463. In still other embodiments, one adjustable loop 451 can loop around the tibial tray 414 while the other adjustable loop 455 is coupled to the suture 463 or directly to the ligament 421.

Subsequently, the first and/or second free ends 453, 457 can be pulled away from the longitudinal passage portion 445 (as represented by two arrows in FIG. 17) in order to reduce the size of the adjustable loops 451, 455, to pull the ligament 421 toward the tibial tray 414, and to increase and adjust tension in the ligament link 419. This can be performed intraoperatively (i.e., during surgery in the operating room). Furthermore, friction between the first and second ends 441, 443 and the longitudinal passage portion 445 can maintain this adjusted level of tension in the ligament link 419.

Figure 18:
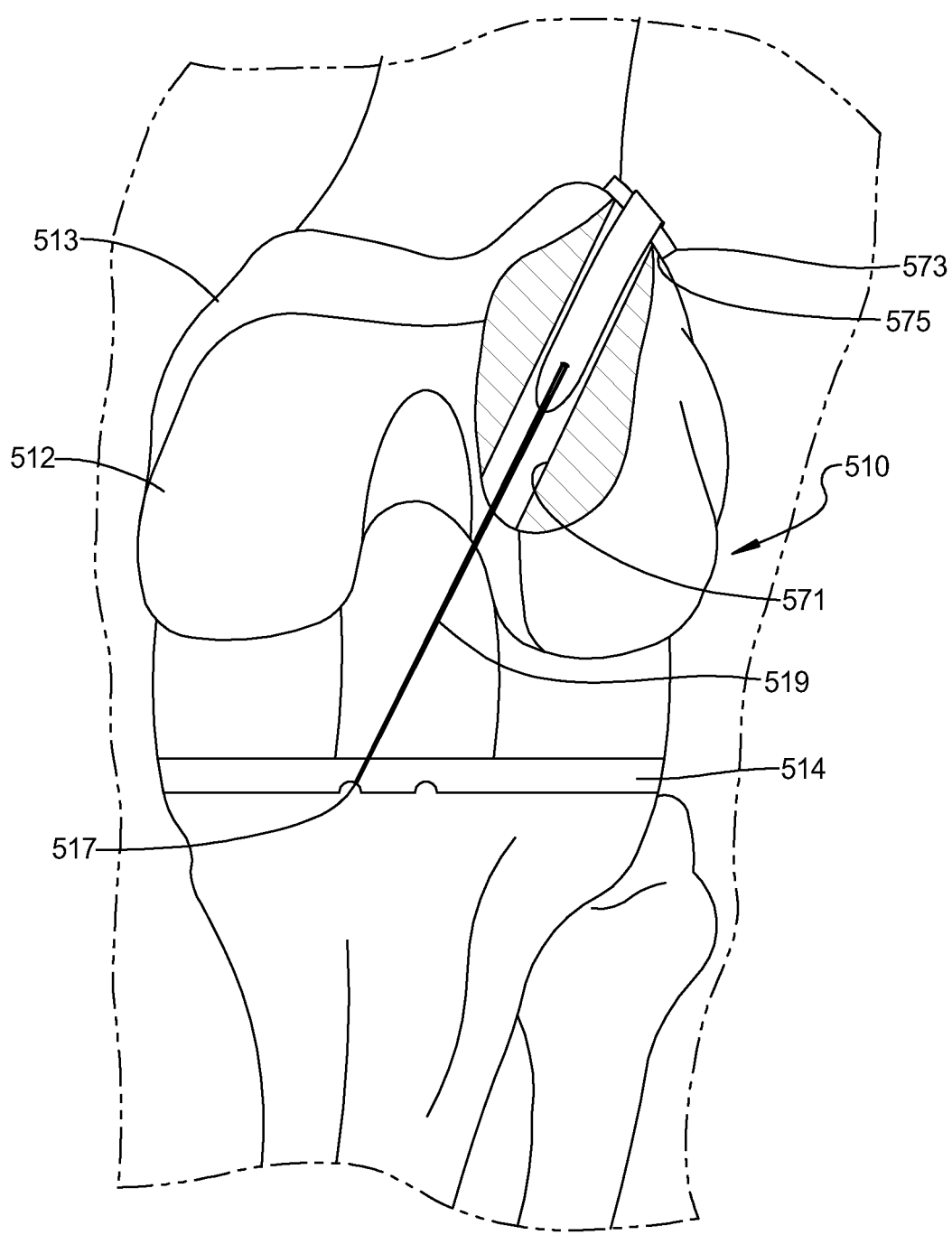
FIG. 18 is an environmental view of the knee prosthesis of FIG. 13 with a partial cutway of a femur according to various other exemplary embodiments.

Referring now to FIG. 18, additional features of the prosthesis assembly 510 will be discussed. Components corresponding to the embodiments of FIGS. 1-8 are indicated with corresponding reference numerals increased by 500.

As shown, the ligament link 519 can extend through a bone tunnel 571 in the femur 513 and can be coupled to the femur 513 via a fastener 573. In some embodiments, the fastener 573 can be seated against an outer rim 575 of the bone tunnel 571. For instance, the fastener 573 can be of a type disclosed in Applicant's co-pending U.S. patent application Ser. No. 12/788,978, filed May 27, 2010, which published as U.S. Patent Publication No. 2010/0292792 on Nov. 18, 2010, which is filed concurrently herewith, and which is entitled PROSTHETIC LIGAMENT SYSTEM FOR KNEE JOINT, which is filed concurrently herewith, and which is hereby incorporated by reference in its entirety. However, it will be appreciated that the fastener 573 can be of any suitable type without departing from the scope of the present disclosure. In some embodiments, the surgeon can select the fastener 573 for implantation from a plurality of different fasteners 573, based on the desired location for attaching the ligament link 519, etc.

Accordingly, as shown in FIG. 18, the ligament link 519 can attach to the femur 513 instead of a resected ligament, as was discussed above in the embodiments of FIGS. 13 and 17. The opposite end of the ligament link 519 can be coupled to the tibial tray 514 similar to the embodiments discussed above. Thus, the ligament link 519 can be received in one of the coupling components 517 of the tibial tray 514.

It will also be appreciated that the femoral component 512 and the tibial tray 514 can be implanted, and the ligament link 519 can be attached to the femur 513 and the tibial tray 514 in a single operative procedure. Accordingly, the knee joint can be repaired more quickly and efficiently, and the patient's recovery time can be reduced.

Referring now to FIGS. 19-21, additional features of the prosthesis assembly 610 will be discussed. Components corresponding to the embodiments of FIGS. 1-8 are indicated with corresponding reference numerals increased by 600.

As shown in FIG. 19, the ligament link coupling component 617 can be operably coupled to (e.g., fixed to) the femoral component 612. For instance, the femoral component 612 can include a first wall 677a and a second wall 677b, each extending superiorly from a respective condyle portion 620, 622. Also, the coupling component 617 can be a rigid rod or bar that is fixed at each end to the condyle portions 620, 622. As such, the coupling component 617 can extend across the intercondylar opening 630. It will be appreciated that the ligament link coupling component 617 can be of any suitable type other than a rod or bar of the type illustrated. For instance, in other embodiments, the ligament link coupling component 617 can be a through hole defined in the first or second walls 677a, 677b, and in some embodiments, the through hole can be reinforced with a grommet-like feature. Also, in some embodiments, the coupling component 617 can be cantilevered within the intercondylar opening 630.

Moreover, the bearing 616 can be a uniform member that is disposed inferior to both condyle portions 620, 622. The bearing 616 can be fixed to the tibial tray 614 using a fastener (e.g., pin, etc.) or in any other suitable fashion. The bearing 616 can also be moveably supported on the tray 614 in some embodiments. Furthermore, the bearing 616 can include an opening 679 that is disposed inferior to the intercondylar opening 630. The opening 679 can be rounded (e.g., circular, elliptical, etc.), polygonor, or any other shape.

Still further, as shown in FIGS. 19-21, the tibial tray 614 can include at least one or more openings 681a, 681b. The openings 681a, 681b can be through holes. The tibial tray 614 can include any suitable number of openings 681a, 681b. For instance, in the embodiments shown, the tibial tray 614 can include two openings 681a, 681b disposed on opposite sides of a medial plane of the tibial tray and disposed on opposite sides of the stem 683. Also, as shown in FIG. 21, the openings 681a, 681b can each extend at a positive, acute angle θ relative to the medial plane P of the tibial tray 614. For instance, each opening 681a, 681b can extend inferiorly from the superior side 668 of the tibial tray 614 generally away from the medial plane P at the angle θ. Moreover, as shown in FIG. 20, the openings 681a, 681b can each extend at a positive, acute angle θ' relative to a coronal plane P' of the tibial tray 614.

When assembled (FIG. 20), a ligament link 619 can be operably coupled to (e.g., at least partially wrap around) the coupling component 619. Also, the ligament link 619 can extend through the opening 679 of the bearing 616. Likewise, the ligament link 619 can extend through one of the openings 681a, 681b of the tibial tray 614. Still further, the ligament link 619 can extend through a bone tunnel 685 formed within the tibia 615 and can operably couple to the tibia 615 via a fastener 673 of the type described above.

It will be appreciated that the surgeon or another medical professional can choose any one of the openings 681a, 681b for receiving the ligament link 619. For instance, in the embodiment shown, the ligament link 619 passes through the opening 681a. This decision can be based on various factors. For instance, in some embodiments, the opening 681a is utilized if the prosthesis assembly 610 is implanted in a left leg, and the opening 681b is utilized if the prosthesis assembly 610 is implanted in a right leg.

Also, it will be appreciated that the angles θ, θ' of the opening 681a, 681b can allow the ligament link 619 to extend through the opening 681a, 681b in a relatively straight line. Moreover, it will be appreciated that the openings 681a, 681b can be positioned on the tibial tray 614 such that the ligament link 619 can be routed in a manner that substantially mimics a natural anatomical ligament. However, it will be appreciated that the openings 681a, 681b can have any suitable location on the tray 614 and can have any suitable shape without departing from the scope of the present disclosure.

In addition, it will be appreciated that the ligament link 619 can attach to the tibia 615 in any suitable fashion other than the bone tunnel 685 and the fastener 673. For instance, in some embodiments, a resected anatomical ligament (not shown) can remain anatomically attached to the tibia 615, and the ligament link 619 can operably couple the resected anatomical ligament to the femoral component. More specifically, in some embodiments, the opening 681a, 681b can provide access to the resected anatomical ligament.

It will be appreciated that the ligament link 19, 319, 419, 519, 619 can include additional sutures, grafts, fasteners, and other components for attachment purposes. For instance, in some embodiments, the ligament link 19, 319, 419, 519 can be attached to the tibial tray 14, 314, 414, 514 via a suture. Additionally, in some embodiments, the ligament link 619 can be attached to the femoral component 612 via a suture. Also, in some embodiments, the ligament link 19, 319, 419, 519 can be attached to the femur or tibial tray 14, 314, 414, 514 via an autograft or other type of graft. Furthermore, in some embodiments, the ligament link 619 can be attached to the tibia 615 or femoral component 612 via an autograft or other type of graft.

Thus, the knee prosthesis assembly 10, 210, 310, 410, 510, 610 can be quickly and conveniently implanted. The ligament link 19, 319, 419, 519, 619 can be conveniently and securely attached to the tibial tray 14, 314, 414, 514 or femoral component 612 for supporting movement of the knee joint. Additionally, tension in the ligament link 19, 319, 419, 519, 619 can be quickly and conveniently adjusted.

As used herein, the terms superior, superiorly, superior direction are used to generally refer to the anatomical meaning, such as higher in place or position or generally situated above. Similarly, the terms inferior, inferiorly, inferior direction are used to generally refer to the anatomical meaning, such as lower in place or position or generally situated below.

Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims. For instance, the sequence of the blocks of the method described herein can be changed without departing from the scope of the present disclosure.

What is claimed is:

1. A prosthetic knee joint assembly for a knee joint with a tibia and a femur, the prosthetic knee joint assembly comprising:
   a unitary, single body femoral component that is adapted to engage the femur;
   at least one bearing that supports articulation of the femoral component thereon;
   a unitary, single body tibial tray that supports the at least one bearing and that is adapted to engage the tibia;
   a ligament link coupling component included directly on one of the femoral component or the tibial tray; and
   a ligament link operably coupled to the one of the femoral component or the tibial tray via the ligament link coupling component, the ligament link also extending through the other of the femoral component or the tibial tray to operably couple to the respective one of the femur or the tibia, the ligament link extending from a first end to a second end, the ligament link having an outer wall defining an interior longitudinal passage portion, the ligament link also having a first aperture passing through the outer wall and disposed between the first and second ends, the ligament link additionally having a second aperture passing through the outer wall and disposed between the first and second ends, the first end extending through the first and second apertures and the longitudinal passage portion to define a first adjustable loop, the second end extending through the first and second apertures and the longitudinal passage portion to define a second adjustable loop.

2. The prosthetic knee joint assembly of claim 1, wherein the first end also includes a first free end, wherein the second end also includes a second free end, the first free end pullable to reduce a size of the first adjustable loop, the second free end pullable to reduce a size of the second adjustable loop.

3. The prosthetic knee joint assembly of claim 1, wherein the first and second adjustable loops are adjustable to change a tension in the ligament link.

4. The prosthetic knee joint assembly of claim 1, wherein the ligament link coupling component is included on the tibial tray and includes a through hole that receives an adjustable loop of the ligament link.

5. The prosthetic knee joint assembly of claim 4, wherein the ligament link coupling component has an axis that extends through a superior surface of the tibial tray and through an inferior surface of the tibial tray.

6. The prosthetic knee joint assembly of claim 1, wherein the ligament link coupling component is included on the tibial tray and includes a groove that nestingly receives a portion of the ligament link.

7. The prosthetic knee joint assembly of claim 6, wherein the tibial tray includes an inferior, anterior edge, and wherein the groove is defined on the inferior, anterior edge.

8. The prosthetic knee joint assembly of claim 6, wherein the groove has an axis that is adapted to be disposed at a positive, acute angle relative to a longitudinal axis of the tibia.

9. The prosthetic knee joint assembly of claim 1, wherein the ligament link coupling component is disposed on an anterior portion of the tibial tray.

10. The prosthetic knee joint assembly of claim 1, wherein the ligament link coupling component is included on the tibial tray, the ligament link coupling component including an eyelet that selectively closes to secure the ligament link to the tibial tray and that selectively opens to allow the ligament link to move into the eyelet.

11. The prosthetic knee joint assembly of claim 1, wherein the tibial tray includes a first ligament link coupling component and a second ligament link coupling component, the first and second ligament link coupling components spaced apart at a distance from each other.

12. The prosthetic knee joint assembly of claim 11, wherein the tibial tray defines a median plane, and the first and second ligament link coupling components are disposed on opposite sides of the median plane.

13. The prosthetic knee joint assembly of claim 1, wherein the ligament link includes a plurality of braided fibers.

14. The prosthetic knee joint assembly of claim 1, wherein the ligament link coupling component is included on the femoral component, the femoral component including a first condylar portion and a second condylar portion separated at a distance apart to define an intercondylar opening, the ligament link coupling component extending from at least one of the first and second condylar portions into the intercondylar opening.

15. The prosthetic knee joint assembly of claim 1, wherein the ligament link coupling component is included on the femoral component, and wherein the tibial tray defines an opening through which the ligament link extends to couple to the tibia.

16. The prosthetic knee joint assembly of claim 15, wherein the tibial tray defines a first opening and a second opening, the first and second openings disposed on opposite sides of a medial plane of the tibial tray.

17. The prosthetic knee joint assembly of claim 1, wherein the ligament link is adapted to extend through the other of the femoral component or the tibial tray to operably couple directly to the respective one of the femur or the tibia.

18. The prosthetic knee joint assembly of claim 1, wherein the ligament link is adapted to extend through the other of the femoral component or the tibial tray to operably couple to the respective one of the femur or the tibia via a resected anatomical ligament.

19. The prosthetic knee joint assembly of claim 1, wherein the first and second adjustable loops of the ligament link are both coupled to the same one of the femoral component or the tibial tray.

20. A prosthetic knee joint assembly for a knee joint of a patient with a tibia and a femur, the prosthetic knee joint assembly comprising:
    unitary, single body femoral component that is adapted to engage the femur, the femoral component including a medial and lateral condyle portion connected by a patellar track portion, an intercondylar opening defined between the medial and lateral condyle portions;
    at least one bearing that supports articulation of at least one of the medial and lateral condyle portions thereon;
    a unitary, single body tibial tray that supports the at least one bearing and that is adapted to engage the tibia, the tibial tray including a plurality of coupling components, the plurality of coupling components disposed on an anterior portion of the tibial tray, the plurality of coupling components disposed on opposite sides of a medial plane of the tibial tray; and
    a ligament link operably coupled to the tibial tray via one of the coupling components, the ligament link also adapted to couple to the femur, the ligament link extending through the intercondylar opening, the ligament link extending from a first end to a second end and having an outer wall defining an interior longitudinal passage portion, the ligament link also including a first aperture passing through the outer wall and disposed between the first and second ends, the ligament link also including a second aperture passing through the outer wall and disposed between the first and second ends, the first end extending through the first and second apertures and the longitudinal passage portion to define a first adjustable loop and a first free end, the second end extending through the first and second apertures and the longitudinal passage portion to define a second adjustable loop and a second free end, the first and second free ends pullable to increase a tension in the ligament link.

* * * * *